United States Patent
Zamanillo-Castanedo et al.

(10) Patent No.: US 9,931,346 B2
(45) Date of Patent: Apr. 3, 2018

(54) SEROTONIN-NOREPINEPHRINE REUPTAKE INHIBITORS (SNRIS) AND SIGMA RECEPTOR LIGANDS COMBINATIONS

(71) Applicant: LABORATORIOS DEL DR. ESTEVE S.A., Barcelona (ES)

(72) Inventors: Daniel Zamanillo-Castanedo, Barcelona (ES); Enrique Portillo-Salido, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 15/104,384

(22) PCT Filed: Dec. 16, 2014

(86) PCT No.: PCT/EP2014/077996
§ 371 (c)(1),
(2) Date: Jun. 14, 2016

(87) PCT Pub. No.: WO2015/091508
PCT Pub. Date: Jun. 25, 2015

(65) Prior Publication Data
US 2016/0310500 A1 Oct. 27, 2016

(30) Foreign Application Priority Data
Dec. 17, 2013 (EP) .................................... 13382518

(51) Int. Cl.
*A61K 31/5377* (2006.01)
*A61K 45/06* (2006.01)
(Continued)

(52) U.S. Cl.
CPC ........ *A61K 31/5377* (2013.01); *A61K 31/137* (2013.01); *A61K 31/381* (2013.01); *A61K 45/06* (2013.01)

(58) Field of Classification Search
CPC ........................ A61K 31/4523; A61K 31/4725
See application file for complete search history.

(56) References Cited

U.S. PATENT DOCUMENTS

| 2,908,677 A | 10/1959 | Metal Straley |
| 3,514,439 A | 5/1970 | Wehrli Walter et al. |
(Continued)

FOREIGN PATENT DOCUMENTS

| EP | 0248594 A2 | 12/1987 |
| EP | 0414289 A1 | 2/1991 |
(Continued)

OTHER PUBLICATIONS

Davis et al., Diabetes Care, 1999;22(11):1909-1910.*
(Continued)

*Primary Examiner* — San Ming R Hui
(74) *Attorney, Agent, or Firm* — Troutman Sanders LLP

(57) ABSTRACT

The invention refers to a synergistic combination comprising a Sigma ligand of general formula (I), and a Serotonin-Norepinephrine Reuptake Inhibitor (SNRI), a medicament comprising said active substance combination, and the use of said active substance combination for the manufacture of a medicament, particularly for the prophylaxis and/or treatment of pain.

11 Claims, 2 Drawing Sheets

(51) Int. Cl.
*A61K 31/137* (2006.01)
*A61K 31/381* (2006.01)

(56) References Cited

U.S. PATENT DOCUMENTS

| | | |
|---|---|---|
| 3,980,675 A | 9/1976 | Venturella et al. |
| 4,024,175 A | 5/1977 | Satzinger et al. |
| 4,207,392 A | 6/1980 | Shiao et al. |
| 4,234,479 A | 11/1980 | Mennicke et al. |
| 4,234,616 A | 11/1980 | Shu et al. |
| 4,337,263 A | 6/1982 | Techer et al. |
| 5,948,777 A | 9/1999 | Bender et al. |
| 6,057,371 A | 5/2000 | Glennon |
| 6,100,259 A | 8/2000 | Xiang et al. |
| 6,166,072 A | 12/2000 | Bell et al. |
| 6,451,857 B1 | 9/2002 | Hurtt et al. |
| 6,492,529 B1 | 12/2002 | Kapadia et al. |
| 6,509,367 B1 | 1/2003 | Choon-Moon |
| 7,091,257 B2 | 8/2006 | Greer, IV |
| 7,105,646 B2 | 9/2006 | Chamberlain et al. |
| 7,696,199 B2 | 4/2010 | Laggner et al. |
| 7,799,782 B2 | 9/2010 | Munson et al. |
| 7,988,966 B2 | 8/2011 | Pavone |
| 8,193,223 B2 | 6/2012 | Jagerovic et al. |
| 8,293,740 B2 | 10/2012 | Laggner et al. |
| 8,314,096 B2 | 11/2012 | Laggner et al. |
| 8,470,867 B2 | 6/2013 | Laggner et al. |
| 8,492,425 B2 | 7/2013 | Torrens Jover et al. |
| 8,877,753 B2 | 11/2014 | Buschmann |
| 2001/0036951 A1 | 11/2001 | Farrar et al. |
| 2003/0144309 A1 | 7/2003 | Choon-Moon |
| 2005/0020483 A1 | 1/2005 | Oksenberg |
| 2006/0106068 A1 | 5/2006 | Laggner |
| 2007/0208134 A1 | 9/2007 | Hunter et al. |
| 2008/0058362 A1 | 3/2008 | Singh et al. |
| 2008/0125416 A1 | 5/2008 | Laggner et al. |
| 2008/0161604 A1 | 7/2008 | Calvani et al. |
| 2009/0018151 A1 | 1/2009 | Fink |
| 2009/0264442 A1 | 10/2009 | Cuberes-Aitisent et al. |
| 2009/0325975 A1 | 12/2009 | Buschmann |
| 2010/0081659 A1 | 4/2010 | Laggner |
| 2010/0190078 A1 | 7/2010 | Rapaport et al. |
| 2010/0190780 A1 | 7/2010 | Laggner et al. |
| 2010/0190781 A1 | 7/2010 | Laggner et al. |
| 2010/0240711 A1 | 9/2010 | Takada et al. |
| 2011/0112095 A1 | 5/2011 | Buschmann et al. |
| 2011/0269727 A1 | 11/2011 | Toledano |
| 2012/0141606 A1 | 6/2012 | Baeyens-Cabrera et al. |
| 2012/0232093 A1 | 9/2012 | Cuberes-Altisent et al. |
| 2012/0283262 A1 | 11/2012 | Ranzani et al. |
| 2012/0302568 A1 | 11/2012 | Hernandez et al. |
| 2012/0316336 A1 | 12/2012 | Maimo et al. |
| 2013/0109692 A1 | 5/2013 | Hernandez et al. |
| 2013/0143884 A1 | 6/2013 | Cuberes-Aitisent et al. |
| 2013/0158033 A1 | 6/2013 | Hernandez |
| 2013/0324535 A1 | 12/2013 | Zamanillo-Castanedo et al. |
| 2015/0018354 A1 | 1/2015 | Buschmann et al. |
| 2016/0220575 A1 | 8/2016 | Baeyens-Cabrera et al. |

FOREIGN PATENT DOCUMENTS

| | | |
|---|---|---|
| EP | 0431943 A2 | 6/1991 |
| EP | 0445974 A2 | 9/1991 |
| EP | 0518805 A1 | 12/1992 |
| EP | 0529973 A1 | 3/1993 |
| EP | 0441333 B1 | 5/1994 |
| EP | 0975648 A1 | 2/2000 |
| EP | 1130018 A1 | 9/2001 |
| EP | 1634872 A1 | 3/2006 |
| EP | 1634873 A1 | 3/2006 |
| EP | 1829866 A1 | 9/2007 |
| EP | 1829875 A1 | 9/2007 |
| EP | 1847542 A1 | 10/2007 |
| EP | 1787679 A1 | 11/2008 |
| EP | 2090311 A1 | 8/2009 |
| EP | 2112139 A1 | 10/2009 |
| EP | 2113501 A1 | 11/2009 |
| EP | 2116539 | 11/2009 |
| EP | 2353598 A1 | 8/2010 |
| EP | 2254579 A1 | 12/2010 |
| EP | 2353591 A1 | 8/2011 |
| EP | 2361904 A1 | 8/2011 |
| EP | 2415471 A1 | 2/2012 |
| EP | 2292236 A1 | 3/2012 |
| EP | 2335688 A1 | 6/2012 |
| EP | 2460519 A1 | 6/2012 |
| EP | 2460804 A1 | 6/2012 |
| EP | 2524694 A1 | 11/2012 |
| EP | 2395003 A1 | 12/2012 |
| EP | 2426111 A1 | 3/2013 |
| EP | 2426112 A1 | 3/2013 |
| EP | 2792352 A1 | 10/2014 |
| EP | 2818166 A1 | 12/2014 |
| EP | 3043795 A1 | 7/2016 |
| EP | 3082790 A1 | 10/2016 |
| ES | 2251316 A1 | 10/2004 |
| FR | 2301250 A1 | 9/1976 |
| FR | 2472564 A1 | 7/1981 |
| GB | 1088973 A1 | 10/1967 |
| GB | 1496411 A1 | 12/1977 |
| GB | 2026482 A1 | 7/1987 |
| IL | 151533 B | 3/2008 |
| JP | 1992/364129 | 12/1992 |
| JP | 10036259 | 2/1998 |
| JP | 10055048 | 2/1998 |
| JP | 2004/196678 | 7/2004 |
| JP | 2008/510767 | 4/2008 |
| JP | 2008/179541 | 8/2008 |
| RU | 2218187 C2 | 10/2003 |
| RU | 2322977 C1 | 4/2008 |
| RU | 2382646 C1 | 2/2010 |
| SU | 11248 A1 | 9/1929 |
| WO | WO-91/09594 A1 | 7/1991 |
| WO | WO-92/09560 A1 | 6/1992 |
| WO | WO-93/23383 A1 | 12/1992 |
| WO | WO-1996/016063 A1 | 5/1996 |
| WO | WO-1998/046618 A1 | 10/1998 |
| WO | WO-99/01444 A1 | 1/1999 |
| WO | WO-99/21824 A1 | 5/1999 |
| WO | WO-99/31057 A1 | 6/1999 |
| WO | WO-99/31074 A2 | 6/1999 |
| WO | WO-99/31075 A1 | 6/1999 |
| WO | WO-1999/059409 A1 | 11/1999 |
| WO | WO-99/61424 A1 | 12/1999 |
| WO | WO-00/31020 A1 | 2/2000 |
| WO | WO-00/20005 A1 | 4/2000 |
| WO | WO-00/027394 A1 | 5/2000 |
| WO | WO-00/40275 A2 | 7/2000 |
| WO | WO-00/73259 A1 | 12/2000 |
| WO | WO-00/73296 A2 | 12/2000 |
| WO | WO-00/73300 A1 | 12/2000 |
| WO | WO-02/085839 A1 | 10/2002 |
| WO | WO-02/092573 A2 | 11/2002 |
| WO | WO-02/102387 A1 | 12/2002 |
| WO | WO-2003/080183 A1 | 10/2003 |
| WO | WO-2004/016592 A1 | 2/2004 |
| WO | WO-2004/017961 A1 | 3/2004 |
| WO | WO-2004/046129 A2 | 6/2004 |
| WO | WO-2005/061462 A2 | 7/2005 |
| WO | WO-2006/010587 A1 | 2/2006 |
| WO | WO-2006/021463 A1 | 3/2006 |
| WO | WO-2006/027221 A1 | 3/2006 |
| WO | WO2006021462 | 3/2006 |
| WO | WO-2006/118307 A1 | 11/2006 |
| WO | WO-07/002559 A1 | 1/2007 |
| WO | WO-2007/025613 A2 | 3/2007 |
| WO | WO-2007/046550 A1 | 4/2007 |
| WO | WO-07/079086 A1 | 7/2007 |
| WO | WO-2007/090661 A2 | 8/2007 |
| WO | WO-07/098964 A2 | 9/2007 |
| WO | WO-07/108517 A1 | 9/2007 |
| WO | WO-2007/098939 A1 | 9/2007 |
| WO | WO-2007/098953 A1 | 9/2007 |
| WO | WO-2007/098963 A1 | 9/2007 |

(56) References Cited

FOREIGN PATENT DOCUMENTS

| | | |
|---|---|---|
| WO | WO-2007/110221 A1 | 10/2007 |
| WO | WO-2007/141018 A1 | 12/2007 |
| WO | WO-2008/015266 A1 | 2/2008 |
| WO | WO-2008/055932 A1 | 5/2008 |
| WO | WO-2008/108517 A1 | 9/2008 |
| WO | WO-2008/149062 A1 | 12/2008 |
| WO | WO-2009/038112 A1 | 3/2009 |
| WO | WO-2009/071657 A1 | 6/2009 |
| WO | WO-2009/103487 A1 | 8/2009 |
| WO | WO-2009/130314 A1 | 10/2009 |
| WO | WO-2009/130331 A1 | 10/2009 |
| WO | WO2009130310 | 10/2009 |
| WO | WO2011018487 | 2/2011 |
| WO | WO2011064296 | 6/2011 |
| WO | WO2011064315 | 6/2011 |
| WO | WO2011095579 | 8/2011 |
| WO | WO-2011095584 A1 | 8/2011 |
| WO | WO2011095585 | 8/2011 |
| WO | WO2011144721 | 11/2011 |
| WO | WO-2011/147910 A1 | 12/2011 |
| WO | WO-2012/016980 A1 | 2/2012 |
| WO | WO2012019984 | 2/2012 |
| WO | WO-2012/072781 A1 | 6/2012 |
| WO | WO2012072782 | 6/2012 |
| WO | WO2012/156497 | * 11/2012 |
| WO | WO-2012/158413 A1 | 11/2012 |
| WO | WO2012156497 | 11/2012 |
| WO | WO-2014/170319 A1 | 10/2014 |
| WO | WO-2014/207024 A1 | 12/2014 |
| WO | WO-2015/036470 A1 | 3/2015 |
| WO | WO-2015/091505 A1 | 6/2015 |
| WO | WO-2015/091508 A1 | 6/2015 |

OTHER PUBLICATIONS

"Chemotherapy at home, pain and its treatment", Soins, Office De Publicite Generale, Paris, FR, (Sep. 1, 1989), No. 528, ISSN 0038-0814, pp. 17-20, XP009107313 [A] 1-16. * p. 19 *.

Aapro, M. et al., "Anticipatory Nausea and Vomiting", Support Care Cancer, 2005, vol. 13, pp. 117-121.

Abadias, M. et al. "Saftey, Tolerability and Pharmacokinetics of Single and Multiple Doses of a Novel Sigma-1 Receptor Antagonist in Three Randomized Phase I studies," British Journal of Clinical Pharmacology, 2012, 75:1, 103-117.

Abbott, C, A., et al., "The North-West Diabetes Foot Care Study: incidence of, and risk factors for, new diabetic foot ulceration in a community-based patient cohort", Diabetic Medicine, vol. 19, 2002, pp. 377-384.

Abraham, D.J., et al., "Burger's Medicinal Chemistry: Drug Discovery and Development" 7th edition, 8 vol. set, 2010.

Abrams, P., et al., "The standardisation of terminology of lower urinary tract function: report from the standardisation sub-committee of the International Continence Society", Neurology and Urodynamics, 21, 2002, pp. 167-178.

Acta Obstetrica Gynecologica Japonica, 2000, vol. 52 (6), pp. 117-120.

Advokat, C., et al., "Selective antinociceptive effect of excitatory amino acid antagonists in intact and acute spinal rats," Pharmacology Biochemistry and Behavior 51(4):855-60 1995.

Alberts, D.S., et al., "Cisplatin-associated neurotoxicity: can it be prevented?" Anti-cancer Drugs, 1995, vol. 6, pp. 369-383.

Almerico, AM., "1-Methyi-3H-pyrazolo[1, 2-a]benzo[1, 2, 3, 4] tetrazin-3-ones: Design, synthesis and biological activity of new antitumor agents", Journal of Medicinal Chemistry, vol. 48, 2005, pp. 2859-2866.

Anderson, B.D. et al., "Preparation of Water-Soluble Compounds Through Salt Formation" The Practice of Medicinal Chemistry, Chapter 34, pp. 739-754.

Angst, M.S., et al., "Opioid-induced Hyperalgesia: A Qualitative Systematic Review," Anesthesiology. vol. 104 pp. 570-587 (2006).

Anonymous "Opioid-Induced hyperalgesia," http://web.archive.org/web/20080712205531/http://en.wikipedia.org/wiki/Opioid-inducedhyperalgesia (retrieved Feb. 16, 2017).

Anton, E., "Delayed toxicity of cyclophosphamide on the bladder of DBA/2 and C57BL/6 female mouse," Int. J. Exp. Path., 83, 2002, pp. 47-53.

Arafa, et. al., Journal of Medicinal Chemistry, 2005, American Chemical Society, vol. 48, pp. 5480-5488.

Argyrioul, A.A., et al., "Bortezomib-induced peripheral neuropathy in multiple myeloma: a comprehensive review of the literature", Blood, 2008, vol. 112, No. 5, pp. 1593-1599.

Arthritis [online], [retrieved on Nov. 20, 2007]. Retrieved from the Internet, URL; http://www.nlm.nih.gov/medlineplus/ency/article/001243.htm>.

Asano, T., et al. Antinociception by epidural and systemic alpha(2)adrenoceptor agonists and their binding affinity in rat spinal cord and brain, *Anesth Anal g.* 2000; 90 (2): 400-407.

Baraldi, et al., "Ethyl 2, 4-Dioxoalkanoates as Starting Materials for a Convenient Route to 3(2H)Furanones and 3(2H) Furanimines", Tetrahedron, vol. 43, No. 1, pp. 235-242, 1987.

Baraldi, et al., "Ethyl 5-Substituted-3-Isoxazolecarboxylates as Starting Materials for a Convenient Route to 3(2H) Furanones and 3(2H)Iminofuranes", Tetrahedron Lett., 25(38), pp. 4313-4316; 1984.

Barnes, J.M. et al., "Reserpine, *Para*-Chlorophenylalanine and Fenfluramine Antagonise Cisplatin-Induced Emesis in the Ferret", Neuropharmacology, 1988, vol. 27, No. 8, pp. 783-790.

Batson, et al., "a-Hydroxy Cyclopentenones from a-Diketones", Organic Letters, vol. 7, No. 13, pp. 2771-2774, 2005.

Beaudegnies, R., et al. "Design and synthesis of novel spirocyclopropyl cyclohexane-1,3-diones and -1,3,5-triones for their incorporation into potent HPPD inhibitors", Tetrahedron Letters, 2010, vol. 51, pp. 2741-2744.

Bennett, G. J. "Pathophysiology and Animal Models of Cancer-Related Painful Peripheral Neuropathy", The Oncologist, 2010, 15 (supp12), pp. 9-12.

Berge, S.M. et al., "Pharmaceutical Salts," Journal of Pharmaceutical Sciences, 1977, vol. 66, No. 1, pp. 1-19.

Bon, K., et al., "Characterization of cyclophosphamide cystitis, a model of visceral and referred pain, in the mouse: species and strain differences.", J UROL., (2003), vol. 170, No. 3, pp. 1008-1012.

Boulton, A.J.M., et al., "Diabetic Neuropathies" Diabetes Care, vol. 28, No. 4, Apr. 2005, pp. 956-962.

Bowen W. D., Pharmaceutica *Acta Helvetiae*;2000; 74:211-218.

Brammer et al. In European Journal of Pharmacology, 553, 141-145 (2006).

Brennan, T.J., et al., "Characterization of a rat model of incisional pain", Pain, 1996, vol. 64, pp. 493-501.

Brussee, et al., Diabetes, 2008, 57: 1664-1673, "Distal Degenerative Sensory Neuropathy in a Long-Term Type 2 Diabetes Rat Model".

Kautio, et al., "Amitriptyline in the Prevention of Chemotherapy-induced Neuropathic Symptoms" (2009) Anticancer Research, 29:2601-2606.

Kautio, et al., "Amitriptyline in the Treatment of Chemotherapy-Induced Neuropathic Symptoms" (2008) Journal of Pain and Symptom Management, 35(1) :31-39.

Bryant et al., Opioids and addiction: Emerging pharmaceutical strategies for reducing reward and opponent processes, Clinical Neuroscience Research, 2005, 5, pp. 103-115.

Buerkle, H., Yaksh, T. L. Pharmacological evidence for different alpha 2-adrenergic receptor sites mediating analgesia and sedation in the rat, *Br J Anaesth*. 1998; 81 (2): 208-215.

Bura, S.A. et al., "Evaluation of the Effect of the Selective Sigma-1 Receptor Antagonist SIRA in Neuropathic Pain Using an Operant Model", Eur J. Pain Supplements 2010, vol. 4, p. 49 (Abstract Only).

Buvanendran, A., et al. "Characterization of a New Animal Model for Evaluation of Persistent Postthoracotomy Pain", Anesth Analg, 2004, vol. 99, pp. 1453-1460.

Cancer [online], [retrieved on Jul. 6, 2007]. Retrieved from the Internet, URL; http://www.nim.nih.gov/medlineplus/cancer.html>.

Cancer and Metastasis Reviews, 17(1), 91-106, 1998.

(56) References Cited

OTHER PUBLICATIONS

Cao, J., et al., "Dual Probes for the Dopamine Transporter and sigmal Receptors: Novel Piperazinyl Alkyl-bis(4-fluorophenyl)amine Analogues as Potential Cocaine-Abuse Therapeutic Agents", J. Med. Chem, No. 13, Mar. 20, 1946, pp. 2589-2598.

Carlsson, et al., "Interaction of pentobarbital and morphine in the tail-ftick test performed on rates: synergism at the spinal and antagonism at the supraspinal level", NeuroSci. Lett.; 1986; 71; pp. 356-360.

Carrie, et al., Int Orthopaedics vol. 30, pase 445-451. publication year: 2006.

Bryans, J.S., et al., "3-substituted GABA analogs with central nervous system activity: a review," Med Res Rev, 19, 1999, pp. 149-177.

Case 07 "Joint Pain and Muscle Pain", Nurse Beans—Smart Nurse, Nov. 2007, vol. 9, No. II, pp. 1238-1239.

Celerier, et al., "Progressive Enhancement of Delayed Hyperalgesia Induced by Repeated Heroin Administration: A Sensitization Process," The Journal of Neuroscience. vol. 21, No. 11 pp. 4074-4080 (2001).

Cepeda, MS, "Comparison of Morphine, ketorolac, and their combination for postoperative pain: results form a large, randomized, double-blind trial", anesthesiology, 2005, vol. 103, No. 6, pp. I225-I232.

Cersosimo, R.J., "Oxaliplatin-Associated Neuropathy: A Review", The Annals of Pharmacotherapy, 20051 vol. 39 pp. 128-135.

Chaplan S. R., et al., "Quantitative assessment of tactile allodynia in the rat paw", J. Neurosci. Methods, (1994), vol. 53, pp. 55-63.

Chaudhry, V., et al., "Bortezomib and thalidomide-induced subacute demyelinating polyneuropathy," Clinical Neurophysiology, 2009, vol. 120, p89-e126.

Chaudhry, V., et al., "Peripheral Neuropathy from Taxol and Cisplatin Combination Chemotherapy: Clinical and Electrophysiological Studies", Annals of Neurology, 1994, vol. 35, No. 3, pp. 304-311.

Chen, et al., Modern Bone Science, Modern Orthopaedics, "14.2.2 Drug Analgesia," p. 164, 2010, including English translation.

Chen, S.R., et al., "Synergistic Effect between Intrathecal Non-NMDA Antagonist and Gabapentin on Allodynia Induced by Spinal Nerve Ligation in Rats", Anesthesiology, 2000, vol. 92, pp. 500-506.

Chen, D., et al., "Development and application of rodent models for type 2 Diabetes", Diabetes, Obesity and Metabolism, vol. 7, 2005, pp. 307-317.

Cherny, N., "Opioids and the Management of Cancer Pain", Eur. J. Cancer Supplement 2005, vol. 3, pp. 61-75.

Chichenkov, O.N. et al., "Effect of haloperidol on the analgesic activity of intracisternally and intrathecally injected opiate agonists," Farmakologiya I Toksikologiya, (1985), vol. 48. 48, No. 4, pp. 58-61.

Chien, C., et al., "Sigma antagonists potentiate opioid analgesia in rats," Neuroscience Letters, vol. 190, No. 2, 1995, pp. 137-139.

Chien, et al., "Selective Antagonism of Opioid Analgesia by a Sigma System," J. Pharmacol. Exp. Ther.; 1994; 271; pp. 1583-1590.

Cited ref STN serach abstract JP1 0055048.

Clark, J.B., et al., "The Diabetic Zucker Fatty Rat (41611)", Proceedings of the society for experimental Biology and Medicine, 1983, vol. 173, pp. 68-75.

Consilium MedSigma-receptors: new potentials of the treatment of depressions. Consilium Medicumicum 2012, vol. 14, No. 2 (found in the Internet: URL<new.Consiliummedicum.com/magazines/cm/medicum/article/21505, paragraphs 4-8).

Final Office Action as dated Nov. 29, 2007 in related priority application U.S. Appl. No. 10/978,250.

Final Office Action as dated Oct. 20, 2008 in related priority application U.S. Appl. No. 10/978,250.

Non-Final Office Action as dated Apr. 16, 2008 in related priority application U.S. Appl. No. 10/978,250.

Non-Final Office Action as dated Jun. 14, 2007 in related priority application U.S. Appl. No. 10/978,250.

Requirement for Restriction/Election as dated Apr. 5, 2007 in related priority application U.S. Appl. No. 10/978,250.

Coxon, et al., "Acid-catalysed Rearrangements of trans- and cis-1-Acetoxy-3,4-epoxypentane and 1-Acetoxy-4,5- epoxyhexane", J_Chem_Soc_Chem_Commun., 8, pp. 261-262, 1973.

Crawford, K.W.et al., "Sigma-2 Receptor Agonists Activate a Novel Apoptotic Pathway and Potentiate Antineoplastic Drugs in Breast Tumor cell Lines1," Cancer Research, 2002, vol. 62, pp. 313-322.

D'Amour, F. E. and Smith, D. L. A method for determining the loss of pain sensation, J. Pharmacal. Exp. Ther. 1941; 72:74-79.

Dani, et al. (2007) The local antinociceptive effects of paracetamol in neuropathic pain are mediated by cannabinoid receptors. European Journal of Pharmacology 573(1-3): 214-215.

Danziger, et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London. Series B, Biological Sciences, vol. 236, No. 1283, pp. 101-113.

Daousi, C., et al., "Chronic painful peripheral neuropathy in an urban community: a controlled comparison of people with and without diabetes", Diabetic Medicine, vol. 21, 2004, pp. 976-982.

Dapeng Li "The Role of Glial Cells in . . . Pain", Thesis of Huazhong, University of Science and Technology, 2006, p. 24; Publication Date: Feb. 19, 2008.

Database WPI Week 200451 Thomson Scientific, London, GB; AN 2004-529624-& JP 2004 196678 A (DAINIPPON PHARM CO LTD) Jul. 15, 2004 (Jul. 15, 2004).

Dauben, W., et al., "Organic Reactions at High Pressure Preparation of Wittig Phosphonium Salts at Ambient Temperature", J. Org_Chern., 1984, vol. 49, pp. 4293-4295.

Epstein, et al., "Oral topical doxepin rinse: analgesic effect in patients with oral mucosal pain due to cancer or cancer therapy" (2001) Oral Oncology, 37:632-637.

DeHaven-Hudkins, et al., "Characterization of the binding of [H](+)-pentazocine to σ recognition sites in guinea pig brain," European Journal of Pharmacology- Molecular Pharmacology Section, 1992, vol. 227, pp. 371-378.

Dewar, "Diethyl-[3-(5-methyl-1-phenyl-1H-pyrazol-3-yl)-propyl]amine", Database Beilstein, Beilstein Institute for Organic Chemistry, Frankfurt-Main, DE, Database accession No. 213356, XP002605612 [X] 1-3,5,6,9. * the whole document *.

Dewar, M. J. S., "Attempts to find new Antimalarials. Part XXI", Journal of the Chemical Society, (1944), pp. 615-619.

Dias, V. C., et al., Clinical experience with transdermal clonidine in African-American and Hispanic-American patients with hypertension: evaluation from a 12-week prospective, open-label clinical trial in community-based clinics, Am J Ther. 1999; 6 (1): 19-24.

Diaz, J.L. et al., "Selective Sigma-1 Receptor Antagonists: Emerging Target for the Treatment of Neuropathic Pain", Cent. Nerv. Syst. Agents in Med. Chem. 2009, vol. 9 pp. 172-183.

Dixon, W. J., "Efficient analysis of experimental observations", Ann. Rev. Pharmacal. Toxicol., 20,1980, pp. 441-462.

Dmitrieva, N., et al., "The role of nerve growth factor in a model of visceral inflammation", Neuroscience, vol. 78, No. 2, 1997, pp. 449-459.

Dosen-Micovic, et. al., Bioorganic and Medicinal Chemistry, 2006, Elsevier, vol. 14, pp. 2887-2895.

Dougherty, P.M., et al. "Taxol-induced sensory disturbance is characterized by preferential impairment of myelinated fiber function in cancer patients", Pain, 2004, vol. 109, pp. 132-142.

Drug encyclopedia M., RLS 2001, pp. 572-573, articles "Morphine", "Morphine Sulfate".

Du, J., et al. "Kainate-induced Excitation and Sensitization of Nociceptors in Normal and Inflamed Rat Glabrous Skin", Neuroscience, 2006, vol. 137, pp. 999-1013.

Dukic-Ott, A. "Production of pellets via extrusion spheronisation without the incorporation of microcrystalline cellulose: A critical review," European Journal of Pharmaceutics and Biopharmaceutics, 2009, vol. 71, pp. 38-46.

(56) References Cited

OTHER PUBLICATIONS

Dunlap, B., et al., "Chemotherapy-Induced Peripheral Neuropathy Measurement", The Journal of Supportive Oncology, 2006, vol. 4, 8, pp.

Dworkin R.H., "An Overview of Neuropathic Pain: Syndromes, Symptoms, Signs, and Several Mechanisms," The Clinical Journal of Pain 2002, vol. 18, pp. 343-349.

Dworkin, R.H. et a., "Recommendations for !he Pharmacological Management of Neuropathic Pain: Literature Update", Mayo Clin. Proc., 2010, 85(3)(Suppl), S3-S14.

Effenberger, F., et al., Chern. Ber., 102(10), 3260-3267, 1969.

Eghbaldar, et al., "Substances aromatisantes separation chirale par chromatographie gazeuse" Parfums, Cosmetiques, Aromes, 104, pp. 71-78, 1992.

Eisenach, J. C., et al., Intrathecal, but not intravenous, clonidine reduces experimental thermal or capsaicin-induced pain and hyperalgesia in normal volunteers; *Anesth Analg*; 1998; 87: 591-596.

Entrena, J.M., et al., "Sigma-I receptors are essential for capsaicin-induced mechanical hypersensitivity: Studies with selective sigma-1 ligands and sigma-1 knockout mice", PAIN, (2009), vol. 143, pp. 252-261.

Epilepsy [online], [retrieved on Nov. 20, 2007]. Retrieved from the Internet, URL; http://www .nim.nih.gov/medlineplus/ency/article/000694.htm>.

Botting, R.M.; Clinical Infectious Diseases, 2000, 31, S202-10.

Stubblefield, et al., "Upper-Extremity Pain Disorders in Breast Cancer" (2006) Arch Phys Med Rehabil, vol. 87, Suppl 1, pp. S96-S99.

Falk et al. "Pain and Nociception: Mechanisms of Cancer-Induced Bone Pain", Journal Clinical Oncology, 2014, vol. 32, pp. 1647-1654.

Wickham, "Chemotherapy-Induced Peripheral Neuropathy: A Review and Implications for Oncology Nursing Practice" (2007) Clinical Journal of Oncology Nursing, vol. 11, No. 3, pp. 361-376.

Finnerup, N.B., et al. "The evidence for pharmacological treatment of neuropathic pain", Pain, 2010, vol. 150, pp. 573-581.

Forsyth, P.A., et al., "Prospective study of paclitaxel-induced peripheral neuropathy with quantitative sensory testing", Journal of Neuro-Oncology, 1997, vol. 35, pp. 47-53.

Friedman, J.E., et al., Altered expression of muscle glucose transporter GLUT -4 in diabetic fatty Zucker rats (ZDF/Drtfa), American Physiological Society, 1991, E782-E788.

Gabriel, A.F., Preoperative housing in an enriched environment significantly reduces the duration of post-operative pain in a rat model of knee inflammation, Neurosci. Lett. 2010, vol. 469, No. 2, pp. 219-232.

Gauchan, P., et al., "Mechanical Allodynia Induced by Pacli taxel, oxaliplatin and Vincristine: Different Effectiveness of Gabapentin and Different Expression of Voltage-Dependent Calcium Channel a26-1 subunit", Biol. Phann. Bull., 2009, vol. 32, No. 4 f pp. 732-734.

Gentili, M., et al., Intra-articular morphine and clonidine produce comparable analgesia but the combination is not more effective, *Br J Anaesth*. 1997; 79 (5): 660-661.

Glass et al., "Evaluation of pentamorphone in humans: a new potent opiate," Anesth. Analg. Mar. 1989, 68(3) 302-7.

Goblirsch, M.J., et al., "Biology of Bone Cancer Pain," Clin. Cancer Res. 2006, vol. 12 (20 Suppl.), pp. 6231s-6235s.

Goodman, et al., "The Pharmacological Basis of Therapeutics", 8th Ed.; 13-18, 1992.

Gordois, A., et al., "The Health Care Costs of Diabetic Peripheral Neuropathy in the U.S.", Diabetes Care, vol. 26, No. 6, Jun. 2003, pp. 1790-1795.

Gordon, A.N., et al., "Phase 1 Dose Escalation of Paclitaxel in Patients with Advanced Ovarian Cancer Receiving Cisplatin: Rapid Development of Neurotoxicity is Dose-Limiting", Journal of Clinical Oncology, 1997, vol. 15, No. 5, pp. 1965-1973.

Gotub et al., "Molecular Classification of Cancer: Class Discovery and Class Prediction by Gene Expression Monitoring," Science, 286: 531-537, 1999.

Grahame-Smith, D.G., et al., Oxford textbook on clinical pharmacology and drug therapy M., "Meditsina", 2000, pp. 658-661, Chapter "Narcotic analgesics".

Gralla et al. In Annals of Internal Medicine 95(4), 414-420 (1981).

Grover, S., et al., "Role of inflammation in bladder function and interstitial cystitis", Therapeutic Advances in Urology, 3(1 ), 2011, pp. 19-33.

Grunberg, S, M., et al., "Incidence of Chemotherapy-Induced Nausea and Emesis after Modern Antiemetics," Cancer, 2004, vol. 100, pp. 2261-2268.

Guignard, et al., "Acute Opioid Tolerance: Intraoperative RemifentanilIncreases Postoperative Pain and Morphine Requirement," Anesthesiology, vol. 93 pp. 409-417 (2000).

Guitart, X., et al., "Sigma receptors biology and therapeutic potential", Psychophamacology, 2004, vol. 17 4, pp. 301-319.

Haleblian, "Characterization of Habits and Crystalline Modification of Solids and Their Pharmaceutical Applications," Journal of Pharmaceutical Sciences, vol. 64, No. 8 pp. 1269-1288 (1975).

Hall, J. E., Uhrich, T. D., Ebert, T. J. Sedative, analgesic and cognitive effects of clonidine infusions in humans, *Br J Anaesth*. 2001; 86 (1 ): 5-11.

Díaz, J.L., et al., "Synthesis and Biological Evaluation of the 1-Arylpyrazole Class of sigma 1 Receptor Antagonists," Journal of Medicinal Chemistry, (Oct. 11, 2012), vol. 55, No. 19, doi:10.1021/jm3007323, ISSN 0022-2623, pp. 8211-8224.

Hancock, et al., "Characteristics and Significance of the Amorphous State in Phamnaceutical Systems," Journal of Phamnaceutical Sciences, vol. 86, No. 1 pp. 1-12 (1997).

Hanner, et al., "Purification, molecular cloning, and expression of the mammalian sigma1-binding site," Proc. Natl. Acad. Sci., USA, Jul. 1996, vol. 93, pp. 8072-8077.

Hanno, Philip, "International Consultation on IC—Rome, Sep. 2004/Forging an interenational consensus: progress in painful bladder syndrome/interstitial cystitis", Int Urogynocol J, 16, 2005, pp. S2-S34.

Harden, N., et al., "Unmet Needs in the Management of Neuropathic Pain", Journal of Pain and Symptom Management, 2003, 25, 5S, S12-S17.

Hartwig, J., "Synthesis, Structure, and Reactivity of a Palladium Hydrazonato Complex: A New Type of Reductive Elimination Reaction to FormC-N Bonds and Catalytic Arylation of Benzophenone Hydrazone", Angew. Chem. Int. Ed., 1998, vol. 37, No. 15, pp. 2090-2093.

Hayashi, T., et al., "Sigma-1 receptor ligands: potential in the treatment of neuropsychiatric disorders," CNS Drugs. 2004;18(5) :269-84.

Hecht, J. R.' et al., "Prolonged Nausea and Vomiting after High Dose Chemotherapy and Autologous Peripheral Stem Cell Transplantation in the Treatment of High Risk Breast Carcinorrta," Cancer, 19971 vol. 7 9' pp. 1698-1702.

Herrstedt, J., et al., \'Acute emesis moderately emetogenic chemoc. herapy, Support Care Cancer, 2005, vol. 13, pp. 97-103.

Hesketh, M.' et al., "Proposal for classifying the Acute Emetogenicity of Cancer Chemotherapy", Journal of Clinical Oncology, 1997, vol. 15, pp. 103-109.

Hidaka, T., et al., W5-7 "A Basic Study of the Effect Peony Licorice Water on Paclitaxel-Induced Pain in Mice", Japan Academic Journal of Cancer Treatment, Sep. 2009, vol. 44, No. 2, p. 323 [inc. machine English language translation).

Hileman, G.A., et al., "Response surface optimization of high dose pellets by extrusion and spheronization," International Journal of Pharmaceutics, 1993, vol. 100, pp. 71-79.

Hiranita, et al., "Reinforcing effects of sigma-receptor agonists in rats trained to self-administer cocaine," J Pharmacol Exp Ther. Feb. 2010; 332(2):515-524 (2010).

Horner, et al., "Azo-aryle and Phenazine aus primaren Arylaminanionen durch Autoxydation", Chern. Be. 96, pp. 786-793, 1963.

Hsu, et al., Toxic. Appl. Pharmac., vol. 73, No. 3, p. 411-415, 1984.

Hudzik T. J., "Sigma Ligand-Induced Emesis in the Pigeon," Pharmacology Biochemistry & Behavior, 1991, 41(1), pp. 215-217.

(56) References Cited

OTHER PUBLICATIONS

Hudzik, T., et al., "o Receptor-mediated emetic response in pigeons: agonists, antagonists and modifiers", European Journal of Pharmacology, 1993, vol. 236, pp. 279-287.
IASP Classification of Chronic Pain, 2002, 2nd edition, pp. 201-213.
Isakov "The problem of pain in oncology", Russian Medicinal Journal, 2000, vol. 17, pp. 723-727.
Isomers [on-line], [retrieved on Mar. 11, 2007]. Retrieved from the Internet, URL; http://chemed.chem.purdue.edu/genchem/topicreview/bp/1organic/isomers.html>.
Izenwasser, S., et al., "Characterization of kappa-opioid receptor binding in human insular cortex", Life Sciences, Pergamon Press, Oxford, GB, vol. 65, No. 9, Jul. 23, 1999, pp. 857-862.
Janicki, et al., "Detection of Antagonist Activity for Narcotic Analgesics in Mouse Hot-Plate Test" Pharmacol. Biochem. Behavior, 1979; 10(4); pp. 623-626.
Jordan, K., et al. "Chemotherapy-induced nausea and vomiting: current and new standards in the antiemetic prophylaxis and treatment," Eur J Cancer. Jan. 2005;41 (2) :199-205.
Jover, I., et al., "Evaluation, by a Statistically Designed Experiment, of an Experimental Grade of Microcrystalline Cellulose, Avicel 955, as a Technology to Aid to Production of Pellets with High Drug Loading," Journal of Pharmaceutical Sciences, 1996, vol. 85, No. 71 pp. 700-705.
Kaiser, et al., Neurotransmissions; 1991; 7(1); 1-5.
Dugowson, et al.; Phys. Med. Rehabil. Clin. N. Arn. 2006, 17, 347-354.
Hellewell, S.B., et al., "A sigma-likebinding site in rat pheochromocytoma (PC12) cells: decreased affinity for (+)-benzomorphans and lower molecular weight suggest a different sigma receptor form from that of guinea pig brain," Brain Research, vol. 527, pp. 244-253.
Kawamata, M., et al. "Experimental incision-induced pain in human skin: effects of systemic lidocaine on flare formation and hyperalgesia", Pain, 2002, vol. 100, pp. 77-89.
Kehlet, H., et al. "Persistent Surgical Pain: Risk Factors and Prevention," Lancet, 2006, vol. 367; pp. 1618-1625.
Kehlet, H., et al. "PROSPECT: evidence-based, procedure-specific postoperative pain management", Best Practice Res Clin Anaesthesiol., 2007, vol. 21, pp. 149-159.
Kehlet, H., et al., "Anaesthesia, surgery, and challenges in postoperative recovery", Lancet 2003, vol. 362, pp. 1921-1928.
Bryans, J.S., et al., "Identification of novel ligands for the gabapentin binding site on the alpha-2-delta subunit of a calcium channel and their evaluation as anticonvulsant agents", J. Med. Chern. 41, 1998, pp. 1838-1845.
Kenakin, A., Pharmacology Primer, The Evolving Pharmacology of GPCR's, 2006, pp. 27-60.
Kerba, et al. Oct. 2010, Journal of Clinical Oncology, vol. 28, No. 33, pp. 4892-4897.
Herndon, et al.; Pharmacotherapy, 2008, 28(6), 788-805.
Khouzam, H. R., et al., "Remission of Cancer Chemotherapy-Induces Emesis During Antidepressant Therapy with Nefazodone", Psychosomatic Medicine, 1998, vol. 60, pp. 89-91.
Kim, et al., "Activation of the spinal sigma-1 receptor enhances NMDA- induced pain via PKC- and PKA-dependent phosphorylation of the NRI subunit in mice", Br. J. Pharmacal., 2008, vol. 154, pp. 1125-1134.
Kim, et al., Int Neurourol J.; Mar. 2016; 20(1); 13-17.
Kirchmair, R., et al., "Therapeutic Angiogenesis Inhibits or Rescues Chemotherapy-induced Peripheral Neuropathy: Taxol- and Thalidomide-induced Injury of Vasa Nervorum is Ameliorated by VEGF," Molecular Therapy, 2 DD7, pp. 151 No. 1, pp. 69-75.
Koralewski, p., et al., 37 Effectiveness of cyproheptadine in the management of delayed vomiting after cisplatin-based chemotherapy and the assessment of the influence of cyproheptadine on quality of lifen, Chemotherapy Dept. Rydygier Memorial Hospital, Cracow, Poland, vol. 5, pp. 499-503.
Kranz, H., et al., "Drug Release from MCC- and carrageenan-based pellets: Experiment and theory,"European Journal of Pharmaceutics and Biopharmaceutics, 2009, vol. 73, pp. 302-309.
Hinz et al., FASEB Journal, 2007, 7, 2343-2351.
Davies, A., et al., "Functional biology of the alpha-2-delta subunits of voltage-gated calcium channels,"trends in Pharmacological Sciences, vol. 28, No. 5, 2007, pp. 220-228.
Kuruvilla et al., Arch Otolaryngol Head Neck Surg. Jan. 2009; 135(1): 101-105.
Laboratoire Roger Bellon's CAS: 87: 5959, 1977.
LaBuda, et al., (2005) Pharmacological evaluation of the selective spinal nerve ligation model of neuroFathic pain in the rat. J. Neurosci. Methods 144 ( 2) : 175-181.
LaBudde, et al., "The Synthesis of the Mono- and Dihydroxy Derivatives of 1 ,2,5,6- Dibenzanthracene Excreted by the Rabbit and of Other Hydroxylated Dibenzanthracene Derivatives", J. Am. Chern. Soc., 80, pp. 1225-1236, 1958.
Laggner et al. "Discovery of High-Affinity Ligands of Sigma Receptor, ERG2, and Emopamil Binding Protein by Pharmacophore Modeling and Virtual Screening", J. Med. Chem., 2005, vol. 48, pp. 4754-4764.
Langa, et al., "Generation and phenotypic analysis of sigma receptor type I ($\sigma$1) knowckout mice," European Journal of Neuroscience, 2003, vol. 18, pp. 2188-2196.
Laird, J., et al., "Deficits in visceral pain and referred hyperalgesia in Nav1.8 (SNS/PN3)-null mice", The Journal of Neuroscience, 22(19), Oct. 1, 2002, pp. 8352-8356.
Lang, M., et al., "The Use of Polymer Heteronuclei for Crystalline Polymorph selection,"Journal of the American Chemical Society, 2002, vol. 124, No. 50, pp. 14834-14835, SI-S2.
Lau, et al. (2010) Electroacupuncture versus celecoxib for neuropathic pain in rat SNL model. Neuroscience 170 (2): 655-661.
Le Bars, D., et al., Animal models of nociception. Pharmacal. Rev. 2001; 53, 597-652.
Lee, M. et al., "A Comprehensive Review of Opioid-Induced Hyperalgesia," Pain Physician. vol. 14 pp. 145-161 (2011).
Lee, S., et al., "Large-Scale Aspects of Salt Formation: Processing of Intermediates and Final Products", Handbook of Pharmaceutical Salts: Properties, Selection, and use, 2002, Chapter 8, pp. 191-192, 211-214, Chapter 12, 265-266, 282-283.
Levine, J.D. et al., "Desiperamide Enhances Opiate Postoperative Analgesia", Pain, 1986, vol. 27, pp. 45-49.
Li, et al.,"Asymmetric Total Synthesis and Formal Total Synthesis of the Antitumor Sesquiterpenoid (+)-Eremantholide A", Organic Letters, vol. 9, No. 7, pp. 1267-1270, 2007.
Li, et al., "Synthesis and Structure-Antitumor Activity of 4,6-Diamino-1 ,2-Dihydro-2,2-Dimethyi-1-(Substituted Naphthyi-2)-1,3,5-Triazines", Chern. Res. Chinese Univ., 7(3), pp. 197-200, 1991.
Li, F., et al., "Taurine reverses neurological and neurovascular deficits in Zucker diabetic fatty rats," Neurobiology of Disease, vol. 22, 2006, pp. 669-676.
Lippincott's Illustrated Review: Pharmacology, Richard Harvey, 5th, edition published by Wolters Kluwer "Gastrointestinal and Antiemetic Drugs", pp. 351-362.
Lowry, et al., "Protein measurement with the folin phenol reagent," J. Bio.Chem, 1951, vol. 193, pp. 265-275.
Luedtke, R. R., et al., "Neuroprotective effects of high affinity Sigma 1receptor selective compounds," Brain Res. Mar. 2, 2012;1441:17-26.
Luger N.M., et al., "Efficacy of systemic morphine suggests a fundarnen tal difference in the mechanisms that generate bone cancer vs. inflammatory pain", Pain 2002, vol. 99, pp. 397-406.
Luger, N.M., et al., "Bone Cancer Pain: From Model to Mechanism to Therapy", J. Pain and Symp. Manag. 2005, vol. 29 pp. 832-846.
Lytle, et al., "Effects of long-term corn consumption on brain serotonin and the response to electric shock," Science vol. 190, pp. 692-694 (1975).
Mantyh, "Bone cancer pain: From mechanism to therapy", Opin. Support. Palliat. Care, 2014, vol. 8, pp. 83-90.
Mao, J., "Opioid-induced abnormal pain sensitivity: implications in clinical opioid therapy," Pain. vol. 100 pp. 213-217 (2002).

(56) References Cited

OTHER PUBLICATIONS

Mar. 1, 2016 Fourth Office Action, issued in connection with Chinese Patent Application No. 201180065232.X, including English language translation.
Mar. 29, 2016 Office Action, issued in connection with Japanese Patent Application No. 2013-541369, including English translation.
Field, M.J., et al., "Identification of the alpha-2-delta-1 subunit of voltage-dependent calcium channels as a molecular target for pain mediating the analgesic actions of pregabalin", PNAS, vol. 103, No. 46, Nov. 14, 2006, pp. 17537-17542.
Maryanoff, B.E., et al., 37 The Wittig Olefination Reaction and Modifications Involving Phosphoryl-Stabilized Carbanions. Stereochemistry, Mechanism, and Selected Synthetic Aspectsu, Chem. Rev., 1989, vol. 89, pp. 863-927.
Matsumoto RR1, Pouw B. Correlation between neuroleptic binding to sigma(1) and sigma(2) receptors and acute dystonic reactions. Eur J. Phamacol. Aug. 4, 2000;401(2) :155-60.
Max, M.B., et al. "Endogenous Monoamine Analgesic Systems: Amitriptyline in Painful Diabetic Neuropathy", Anesth. Prog., 1987, vol. 34, pp. 113-127.
McGill, J.B., et al.,"l3-Biocker use and diabetes symptom score: results from the GEMINI study", Diabetes, Obesity and Metabolism, vol. 9, No. 3, May 2007, pp. 408-417.
Mega, et al., Experimental Diabetes Research, Jan. 12, 2011, Diabetic Nephropathy Amelioration by a Low-Dose Sitagliptin in an Animal Model of Type 2 Diabetes (Zucker Diabetic Fatty Rat).
Mei, et al., "Receptor Modulation of Opioid Analgesia in the Mouse", J. Pharmacol Exp. Ther.; 2002; 300(4); pp. 1070-1074.
Menten, J., "Co-analgesics and adjuvant medication in opioid treated cancer pain", Eur. J. Cancer Supplement 2005, vol. 3, pp. 77-86.
Mielke, s. et al., "Peripheral neuropathy: A persisting challenge in paclitaxel-based regimes" /European Journal of Cancer, 2006, vol. 42, pp. 24-30.
Ming, L.C., "Screening Polymorphic Forms of Drug Substances by Using Generalized Crystallization Techniques," May 2007 (English language Translation of Abstract).
Moncada A., et al., Effects of serine/threonine protein phosphatase inhibitors on morphine-induced antinociception in the tail flick test in mice. Eur J Pharrnacal. Mar. 28, 2003; 465(1-2): 53-60.
Mosandl, et al., "Stereoisomeric Flavor Compounds XLIV: Enantioselective Analysis of Some Important Flavor Molecules", J. High Resol. Chromatog 13(9), pp. 660-662, 1990.
Mouedden, et al., "Pharmacological evaluation of opioid and non-opioid analgesics in a murine bone cancer model of pain", Pharm. Biochem. And Behavior, 2007, vol. 86, pp. 458-467.
Mueller, et al., "Some Derivatives of 7-Methoxy- and 10-Methoxybenzo (f) quinoline", J. Am. Chem. Soc., 66, pp. 860-862, 1944.
Mukerji, et al., "Addition of Nitrile Oxides to Olefins, Synthesis of Dihydrojasmone and Starting Material for Prostanoids. A Novel Route to Pyrroles", Tetrahedron, 39 (13) pp. 2231-2235, 1983.
Nakajima K., et al., An increase in spinal cord noradrenaline is a major contributor to the antihyperalgesic effect of antidepressants after peripheral nerve injury in the rat. *Pain.* 2012; 153(5): 990.
Nakazato A., et al., "Synthesis and SAR of 1-alkyl-2-phenylethylamine derivatives designed from N,Ndipropyl-4-methoxy- 3-(2-phenylethoxy) phenylethylamine to discover ?lligands", J. Med. Chem., (1999), vol. 42, pp. 3965-3970.
Narujo, Hiroyuki et al., Cancer Pain Treatment—Clinical Oral Morphine Extended-Release Tablets (once/day)—5th, Pharma Medical, 2007, including English language translation.
Nausea and Vomiting (PDQ) Health Professional Version: Prevention and Managemenl of Acute or Delayed Nausea and Vomiting (Emesis). National Cancer Institute. <http://www.cancer.gov/about-cancer/treatment/sideeffects/nausea/nausea-hp-pdq#section/—66>.
Nieto, F. R., et al., "188 A New Selective Sigma-1 Receptor Antagonist (S1RA) Inhibits the Development and Expression of Neuropathic Pain Induced by Paclitaxel in Mice," European Journal of Pain Supplements, vol. 4, No. 1, 2010, p. 56.

Nieto, F.R., et al., "Tetrodotoxin inhibits the development and expression of neuropathic pain induced by paclitaxelin mice", Pain, 2008, vol. 137, pp. 520-531.
Niiyama, et al., "SB366791, a TRPVI antagonist, potentiates analgesic effects of systemic morphine in a murine model of bone cancer pain", Br. J. Anaesth., 2009, vol. 102, pp. 251-258.
Noda, et al., "A Neuroactive Steroid, Dehydroepiandrosterone Sulfate, Attenuates the Development of Morphine Dependence: An Association with Signal Receptors," Neuroscience 2001 Abstract, Presentation No. 668.4, Nov. 2001.
Nomura, M., et al., "Studies on drug dependence (Rept. 322): Attenuation of morphine- and psychostimulants-induced place preference by sigma receptor agonist SA4503", Japanese Journal of Pharmacology, The Japanese Pharmacological Society, Kyoto, JP, vol. 79, No. suppl. 1, Jan. 1, 1999, p. 224P.
O'Brien, C. J., "Recycling the Waste: The Development of a Catalytic Witting Reaction", Agnew. Chern. Int. Ed. 2009, vol. 48, pp. 6836-6839.
Office Action and Search Report corresponding to Taiwanese Patent Application No. 100127236 (Translation) [undated].
Leitner et al., "Regional variation in the ratio of 01 to a2 binding in rat brain," European Journal of Pharmacology, vol. 259, pp. 65-69 (1994).
Official Action corresponding to Japanese Patent Application No. 2013-523580, dated Mar. 31, 2015.
Ohsawa, et al.,"Effect of acute topical application of(+)-pentazocine on the mechanical allodynia in. diabetic mice" Eur. J. Pharmacal., 2010, 641, pp. 49-53.
Olivar, T., et al.,"Cyclophosphamide cystitis in mice: behavioural characterisation and correlation with bladder inflammation", European Journal of Pain, 3, 1999, pp. 141-149.
Oltman, C.L., et al., "Progression of vascular and neural dysfunction in sciatic nerves of Zucker diabetic fatty and Zucker rats", Am. J. Physiol. Endocrinol. Metab., vol. 289, 2005, pp. E113-E122.
Oltman, C.L., et al., "Vascular and neural dysfunction in Zucker diabetic fatty rats: a difficult condition to reverse", Diabetes, Obesity and Metabolism, vol. 10, 2008, pp. 64-74.
Oltman, et al., Treatment of Zucker diabetic fatty rats with AVE7688 improves vascular and neural dysfunction, Diabetes, Obesity and Metabolism, vol. 11, No. 3, 2009, pp. 223-233.
O'Neill, J., et al., Unravelling the rnystery of capsaicin: a tool to understand and treat pain. Pharrnacol Rev. Oct. 2012;64(4) :939-71.
Ongioco, C. D., et al., Alpha2-adrenergic receptors in human dorsal root ganglia: predominance of alpha2b and alpha2c subtype mRNSs, *Anesthesiology* 2000; 92 (4): 968-976.
Osipova, N.A., "Tramadol (Tramal) in the Treatment of Acute and Chronic Pain Syndromes," Russky Meditsinsky Zhurnal (Russian Medicinal Journal), Feb. 25, 2003, No. 4, Sections: Pulmonology: Selected Lectures for Family Physicians (Retrieved from the Internet: URL <rmj.ru/number_36.htm).
Otto, et al., Pain Medicine, 2011, 12: 437-450, "Longitudinal Study of painful Diabetic Neuropathy in the Zucker Diabetic Fatty Rat Model of Type 2 Diabetes: Impaired Basal G-Protein Activity Appears to Underpin Marked Morphine Hyposensitivity at 6 Months."
Owens, N.J. et al., "Antiemetic efficacy of prochlorperazine, haloperidol, and droperidol in cisplatin-induced emesis", Clinical Pharmacy, 1984, vol. 3, pp. 168-170.
Pacharinsak,C., et al., ' "Animal Models of Cancer Pain", Comparative Medicine, 2008, vol. 58, No. 3, pp. 220-233.
Paice, J. A., "Clinical Challenges: Chemotherapy-induced Peripheral Neuropathy", Seminars in Oncology Nursing, 2009, vol. 25, N. 2, Suppl 1, pp. S8-S19.
Palmer, J. L., and Fisch, M. J., "Association Between Symptoms Distress and Survival in Outpatients Seen in a Palliative Care Caner Center", Journal of Pain and Symptom Management, 2005, vol. 29, No. 6, pp. 565-571.
Paquette et al. In Psychopharmacology (Berlin) 204(4):743-754 (2009).
Park, S.B. et al. "Mechanisms Underlying Chemotherapy-Induced Neurotoxicity and the Potential for Neuroprotective Strategies", Current Medicinal Chemistry, 2008, vol. 15, pp. 3081-3094.

(56) References Cited

OTHER PUBLICATIONS

Hammack, et al., "Phase III evaluation of nortriptyline for alleviation of symptoms of cis-platinum-induced peripheral neuropathy" (2002) Pain, 98:195-203.
Petrie, C., et al., "A Novel Biotinylated Adenylate Analogue Derived from Pyrazolou3,4-D 3/4 Pyrimidine for Labeling DNA Probes"Bioconjugate Chemistry, ACS, Washington, DC, US LNKD- DOI :10.1021/BC00012A011, val. 2, No. 6, Nov. 1, 1991 (Nov. 1, 1991) , pp. 441-446, XP0005727891SSN: 1043-1802.
Pirim, A., et al., "Addition of ketamine infusion to patient controlled analgesia with intravenous morphine after abdominal hysterectomy" Agri Jan. 2006; 18(1):52-8 Abstract.
Epstein, et al., "Oral Doxepin Rinse: The Analgesic Effect and Duration of Pain Reduction in Patients with Oral Mucositis Due to Cancer Therapy" (2006) Pain Medicine, vol. 103, No. 2, pp. 465-470.
Polomano, R.C., et al., "Pain and neuropathy in cancer survivors: Surgery, radiation, and chemotherapy can cause pain; research could improve its detection and treatment", Cancer Nursing, Lippincott-Raven Pub., Hagerstown, MD, US, (Mar. 1, 2006), vol. 29, No. 2, suppl, ISSN 0162-220X, pp. 39-47, XP009107315 [A] 1-16 * p. 41, col. R, paragraph 2 ** p. 42, col. R, paragraph 2 *.
Poncelet, A.N., "Risk factors, patterns of presentation, diagnosis, and treatment", Geriatrics, vol. 58, No. 6, Jun. 2003, pp. 16-18, 24-30.
Postma, T.J., et al., "Paclitaxel-induced neuropathy," Annals of Oncology, 1995, vol. 6, pp. 489-494.
Price, et al., J. Am. Chem. Soc., (2005), vol. 127, p. 5512.
Prodrug [online], [retrieved on Mar. 11, 2007. Retrieved from the Internet, URL; http://en.wikipedia.org/wiki/Prodrug>.
Puente, B., et al., "Sigma-1 receptors regulate activity-21 induced spinal sensitization and neuropathic pain after peripheral nerve injury", Pain, 2009, vol. 145, pp. 294-303.
Puskas, F.,et al., Intrathecal clonidine and severe hypotension after cardiopulmonary bypass, *Anesth Analg.* 2003; 97 (5): 1251-1253.
Quasthoff, S., et al., "Chemotherapy-induced peripheral neuropathy," J Neural., 2002, vol. 249, pp. 9-17.
Radesca, et al., "Synthesis and Receptor Binding of Enantimeric N-Substituted cis-N-[2(3,4Dishlorophenyl)ethyl]-2-(1-pyrrolidinyl)cyclohexylamines as High-Affinity σReceptor Ligands," J. Med. Chem., 1991, vol. 34, pp. 3058-3065.
Rao, R.D., et al., "Efficacy of Lamotrigine in the Management of Chemotherapy-induced Peripheral Neuropathy placebo-controlled trial, N01C3", Cancer; 2008, 112(12), 2802-2808.
Raynov, J., "Antiemetics: Side effects and reactions", Archive of Oncology, 2001, vol. 9, No. 3, pp. 151-153.
Kest, et. al., Pharmacology Biochemistry, and Behavior, 1995, Pergamon, vol. 52, No. 1, pp. 175-178.
Perret, D., et al., "Targeting voltage-gated calcium channels for neuropathic pain rnanagernent", Neurotherapeutics: The Journal of the American Society for Experimental NeuroTherapeutics, vol. 6, Oct. 2009, pp. 679-692.
Rodriguez-Spong, B., et al., "General principles of pharmaceutical solid polymorphism: a supramolecular Perspective," Advanced Drug Delivery Reviews, vol. 56 (2004) pp. 241-274.
Roh, D., et al., "Intrathecal Injection of the 01 Receptor Antagonist BD1047 Blocks Both Mechanical Allodynia and Increases in Spinal NR1 Expression during the Induction Phase of Rodent Neuropathic Pain", Anesthesiology, 2008, vol. 109, No. 5, pp. 879-889.
Roila, F., et al., "Delayed emesis: moderately emetogenic chemotherapy", Support Care Cancer, 2005, vol. 13, pp. 104-108.
Roos, et al., Radiotherapy and Oncology, 2003, vol. 67, pp. 207-212.
Rossiter, et al., "Copper (H)-Mediated Arylation with Aryl Boronic Acids for the N-Derivatization ofPyrazole Libraries," J. Comb. Chern., 2004, vol. 6, pp. 385-390, published on web Feb. 5, 2004.
Rouleau, A., et al., "Anti-inflammatory and antinociceptive properites of BP 2-94, a histamine H3-receptor agonist prodrug", The Journal of Pharmacology and Experimental Therapeutics, vol. 295, No. 1, 2000, pp. 219-225.
Rowinsky, E.K. et al., "Phase I and Pharmacologic Study of Paclitaxel and Cisplatin with Granulocyte Colony-25 Stimulating Factor: Neuromuscular Toxicity is Dose-Limiting", Journal of Clinical Oncology, 1993, vol. 11, No. 10, pp. 2010-2020.
Rowinsky, E.K., et al., "Clinical Toxicities Encountered 24 with Paclitaxel (TAXOL)", Seminars in Oncology, 1993, vol. 20, No. 4, suppl. 3, pp. 1-15.
Sabetkasaie, M., et al., "Clonidine and guanfacine-induced antinociception in visceral pain: possible role of alpha2/I2 binding sites", European Journal of Pharmacology, Elsevier Science, NL, (Oct. 6, 2004), vol. 501, No. 1-3, doi:10.1016/J.EJPHAR.2004.08.010, ISSN 0014-2999, pp. 95-101.
Saha, et al., "Spinal Mitogen-Activated Protein Kinase Phosphatase (MKP-3) Is Necessary for the Normal Resolution of Mechanical Allodynia in a Mouse Model of Acute Postoperative Pain", J. Neurosci., 2013, vol. 43, pp. 17182-17187.
Said, G., "Diabetic Neuropathy", Proceedings advanced studies in Medicine, vol. 1, No. 11, Dec. 2001, pp. 457-459.
Sakurada T., et al., Differential effects of intraplantar capsazepine and ruthenium red on capsaicin-induced desensitization in mice. Pharmacal Biochern Behay. Apr. 2003; 7 5 (1): 1 15-21.
Sampson, C., et al., "Effects of imidazoline 12 receptor ligands on acute nociception in rats." Neuroreport Jan. 25, 2012, (Jan. 25, 2012), vol. 23, No. 2, ISSN 1473-558X, pp. 73-77, XP009169909 [Y] 1-15 * See abstract: imidazoline I2 receptor ligands have antinociceptic effect in acute pain *.
Samso, E., et al., Comparative assessment of the anaesthetic and analgesic effects of intramuscular and epidural clonidine in humans, *Can J Anaesth.* 1996; 43 (12): 1195-1202.
Sanchez-Fernandez, C., et al., "Potentiation of morphine-induced mechanical antinociception by sigma-1 receptor inhibition: role of peripheral sigma-1 receptors", Neuropharmacology, 70, 2013, pp. 348-358.
Sandford, M., et al., Pain Physician 2009; 12:679-684.
Sant et al., "The mast cell in interstitial cystitis: role in pathophysiology and pathogenesis,"Urology, 69, Suppl 4A, 2007, pp. 34-40.
Schetz et al. In Brain Research 1181 (2007) 1-9.
Schiff, et al., Nature vol. 277 pp. 665-667. Publication date: Feb. 22, 1979.
Schlegel, T., et al., "Responsiveness of C-fiber nociceptors to punctate force-controlled stimuli in isolated rat skin: lack of modulation by inflammatory mediators and flurbiprofen" Neuroscience Letters, vol. 361, 2004, pp. 163-167.
Schoeffter, et al., "Functional, endogenously expressed 5-hydroxytryptamine 5-ht7 receptors in human vascular smooth muscle cells," British Journal of Pharmacology, 1996, vol. 117, pp. 993-994.
Receveur, Jean-Marie, et al., "Synthesis and biological evaluation of conformationally restricted gabapentin analogues", Bioorganic & Medicinal Chemistry Letters, 9, 1999, pp. 2329-2334.
Seigel, L.J., et al., The Control of Chemotherapy-Induced Emesis, Ann Intern Med. 1981;95(3):352-359.
Selwood, D. L., et al. 37 Synthesis and Biological Evaluation of Novel Pyrazoles and Indazoles as Activators of the Nitric Oxide Receptor, Soluble Guanylate Cyclase, J. Med. Chern, 2001, vol. 44,pp. 78-93.
Sevcik, M.A., et al., "Jlnti-NGF therapy profoundly reduces bone cancer pain and the accompanying increase in markers of peripheral and central sensitization", Pain 2005, vol. 115, pp. 128-141.
Shaw, et al., Proc. Soc. Exp. Biol. Med., (1983), vol. 173, No. 1, pp. 68-75.
Shen, D.M., et al., "Versatile and Efficient Solid-Phase Syntheses of Pyrazoles and Isoxazoles", Organic Letters, 2000, vol. 2, No. 18, pp. 2789-2792.
Shimizu, I., et al., "Effects of AH-9700, (+)-pentazocine, DTG and oxybutynin on micturition in anesthetized rats with acetone-induced cystitis", Life Sciences 69,2001, pp. 1691-1697.
Shimoyama, E., et al., Integrative Medicine you Need to know now "Cancer and Integrative Medicine Palliative Medicine", Modern Physician, Nov. 2008, vol. 28, No. 11, pp. 1605-1607 [inc. machine English language translation].

(56) References Cited

OTHER PUBLICATIONS

Shu, et al., "Parameter Effects on the Thermal Reaction of Cystine and 2,5-Dimethyl-4-hydroxy-3(2H)-furanone", ACS Symposium Letters, 409, pp. 229-241, 1989.
Shvidenko, K.V., et al., "Recyclization Reactions of 2-(1-Benzoylpyrrolidin- 2-Ylidene)Malononitrile", 2010, vol. 46, No. 1, pp. 56-60.
Siau, C., et al., "Dysregulation of Cellular Calcitt.rn Homeostasis in Chemotherapy-Evoked Painful Peripheral Neuropathy", *Anest:h Analg.*, 2006, 102(5), pp. 1485-1490.
Sierralta, F., et al., Alpha-Adrenoceptor and opioid receptor modulation of clonidine-induced antinociception, *Br J Pharmacal.* 1996; 119 (3): 551-554.
Silvererman, M., "Opioid Induced Hyperalgesia: Clinical Implications for the Pain Practitioner," Pain Physician. vol. 12, pp. 679-684 (2009).
Silvey et al. In Journal of Clinical Oncology 6(9), 1397-1400 (1988) (Abstract).
Sima, A.A.F., "The heterogeneity of diabetic neuropathy", Frontiers in Bioscience, May 2008, pp. 4809-4816.
Sima, A.A.F., et al., "A comparison of diabetic polyneuropathy in Type II diabetic BBZDR/Wor rats and in Type I diabetic BBNVor rats", Diabetologia, vol. 43, 2000, pp. 786-793.
Smith, et al., Life Sci., (2004), vol. 74, No. 21, pp. 2593-2604.
Smith, J.C. et al., "Haloperidol: An alternative butyrophenone for nausea and vomiting prophylaxis in anesthesia," AANA Journal 2005, vol. 73, No. 41 pp. 273-275.
Smith, M.T., "Opioid-induced hyperalgesia, opioid rotation and opioid combinations," Acute Pain. vol. 10, pp. 199-200 (2008) [Abstract].
Snyder, et al., "Receptor Mechanisms in Antipsychotic Drug Action: Focus on Sigma Receptors," Journal of Neuropsychiatry, Winter 1989, vol., No. 1, pp. 7-15.
Sonal, G., et al., Ther. Adv. Urol., (2011), vol. 3, No. 1, pp. 19-33.
Souillac, et al., Characterization of Delivery Systems, Differential Scanning Calorimetry, pp. 217-218 (in Encyclopedia of Controlled Drug Delivery, 1999, John Wiley & Sons, pp. 212-227.
Stahl, P.H., et al., "Monographs on Acids and Bases", Handbook of Pharmaceutical Salts: Properties, Selection, and Use, 2002, pp. 265-266, 282-283.
STN—search report—U.S. Appl. No. 11/574,361.
Strupp, et al., "Transdermal fentanyl during high-dose chemotherapy and autologous stem cell support" (2000) Oncology Reports, 7:659-661.
Prasad et al., "Exon-Intron Structure, Analysis of Promoter Region, and Chromosomal Localization of the Human Type 1 Sigma Receptor Gene," Journal of Neurochemistry. vol. 70, pp. 443-451 (1998).
Su, et al., Pharmacology & Therapeutics, vol. 124, pp. 195-206, 2009.
Taylor, C.P., "Mechanisms of analgesia by gabapentin and pregabalin- calcium channel alpha2-delta [Ca v alpha2-delta]ligands", Pain, 142, 2009, pp. 13-16.
Suzuki, Y., et al., "Lowered response threshold and increased responsiveness to mechanical stimulation of cutaneous nociceptive fibers in streptozotocin-diabetic rat skin in vitro—correlates of mechanical allodynia and hyperalgesia observed in the early stage of diabetes", Neuroscience Research, vol. 43, 2002, pp. 171-178.
Tanda, S., et al., "Pains Resistant to Opioids, and Countermeasures thereof~Including Peripheral Neuropathy Measures of Oxaliplatin", Pharmacy, Oct. 2007, vol. 58, No. 11, pp. 2947-2953 [inc. machine English language translation].
Polomano, R.C. , et al., "Chemotherapy-evoked Painful Peripheral Neuropathy", Pain Medicine, 2001, vol. 2, No. 1, pp. 8-14.
Theoharides, T.C., "Mast cell involvement in interstitial cystitis: a review of human experimental evidence," Urology, (2001), vol. 57, No. 6, pp. 47-55.

Tietze, L., et al., Synthesis, (11), 1079-1080, 1993.
Tramer, M. R., et al., "Efficacy and Adverse Effects of Prophylactic Anti emetics during Patient-Controlled Analgesia Therapy: A Quantitative Systematic Review, "Anesth. Analg., 1999, vol. 88, pp. 1354-1361.
Trescot et al., "Opioids in the Management of Chronic Non-Cancer Pain: An Update of American Society of the Interventional Pain Physicians' (ASIPP) Guidelines," Pain Physician. Opioids Special Issue: 11 pp. S5-S62 (2008).
Tyers et al. Oncology 49(4), 263-268 (1992) (Abstract).
Kuloor, et. al., Age and Aging, 2006, Oxford University Press, vol. 35, pp. 639-640.
Van De Merwe, J.P., et al., "Diagnostic criteria, classification, and nomenclature for painful bladder syndrome/interstitial cystitis: an ESSIG proposal", European Urology, 53, 2008, pp. 60-67.
Van Sickle et al. Gastroenterology 121 (4), 767-774 (2001) (Abstract).
Vedejs, E., "Stereochemistry and Mechanism in the Wittig Reaction," Topics in Stereochemistry, 1994, vol. 21, pp. 1-157.
Velucci, "Heterogeneity of Chronic Pain", Clin. Drug Invest. 2012, 32 Suppl. 1, pp. 3-10.
Ventuerello, C., "2-Arylazo-2, 5-dimethyl-3-oxo-2, 3-dihydrof urans, useful intermediates in the synthesis of 1-aryl-5-methyl-3-pyrazolones", Synthesis, 1979, pp. 283-287.
Venturello, C., et al., "A Novel Synthesis of Pyrazol-3-ones Form Biacetyl Dimer and Arenediazonium Salts", Journal of the Chemical Society, Perkin Transactions: Organic and Bio-organic Chemistry, (1972-1999), 7, 681-685, 1978.
Vileikyte, L., et al., Psychological aspects of diabetic neuropathic foot complications: an overview, Diabetes/Metabolism Research and Reviews, vol. 20 (Supp/1), pp. S13-S18.
Vinik, A., et al., Nature Clinical Practice Endocrinology & Metabolism, (2006), vol. 2, pp. 2-13.
Vippagunta, et al., Crystalline solids, Advanced Drug Delivery Reviews, 48: 1-26, 2001.
Virmani, et al., Indian Journal of Chemistry, Section B:Organic Chemistry Including Medicinal Chemistry,vol. 17, 1979, pp. 472-477.
Virmani, V. et al., "Methyl-{3-[5-(4-nitro-phenyl)-1-phenyl-1H-pyrazol-3-yl]propyl}-amine", Database Beilstein, Beilstein Institute for Organic Chemistry, Frankfurt-Main, DE, Database Accession No. 705147, XP002605613 [X] 1-3,9 * the whole document *.
Virmani, V. et al., "Methyl-{4-[5-(4-nitro-phenyl)-1-pheny1-1H-pyrazol-3-yl]-butyl}amine", Database Beilstein, Beilstein Institute for Organic Chemistry, Frankfurt-Main, DE, Database accession No. 706821, XP002605614 [X] 1-3,9 * the whole document *.
Virmani, V. et al., "Methyl-{5-[5-(4-nitro-phenyl)-1-phenyl-1H-pyrazol-3-yl]-pentyl}-amine", Database Beilstein, Beilstein Institute for Organic Chemistry, Frankfurt-Main, DE, Database accession No. 710983, XP002605615 [X] 1-3,9 * the whole document *.
Vorobeychik, et al., "Combination Therapy for Neuropathic Pain—A Review of Current Evidence," CNS Drugs, 2011, pp. 1-12.
Wagaw, S., et al. "A Palladium-Catalyzed Strategy for the Preparation of Indoles: A Novel Entry Into the Fischer Indole Synthesis", J. American Chemical Society, 1998, vol. 120, pp. 6621-6622.
Walker, et al., "Sigma Receptors: Biology and Function," Pharmacological Review, 1990, vol. 42, No. 4, pp. 355-402.
Wang, "Opioid-induced hyperalgesia", Chinese Journal of Pain Medicine, 14(3), pp. 129-130 (2008).
Wantuch, C., et al., "Pharmacological validation of a model of cystitis pain in the mouse", Neuroscience Letters, 421, 2007, pp. 250-252.
Wasserheit, C., et al., "Phase II trial of paclitaxel and cisplatin in women with advanced breast cancer: an active regimen with limiting neurotoxicity", Journal of Clinical Oncology, 1996, vol. 14, No. 7 pp. 1993-1999.
Weetman, A.P., "Graves' hyperthyroidism: how long should antithyroid drug therapy be continued to achieve remission?", Nature Clinical Practice Endocrinology and Metabolism, vol. 2, No. 1, Jan. 2006, pp. 2-3.

(56) References Cited

OTHER PUBLICATIONS

Werling, L.L. et al., "A comparison of the binding profiles of dextromethorphan, memantine, fluoxotine and amitriptyline: treatment of involuntary emotional expression disorder," Exp Neurol. Oct. 2007;207 (2):248-57.
Whittington, C.M., et al., 37 Understanding and utilizing mammalian venom via a platypus venom transcriptome. J. Proteomics 2009; 72; 155-164.
Quirion, et al., "A proposal for the classification of sigma binding sites," Trends Pharmacol. Sci., 1992 vol. 13, pp. 85-86.
Wild, S., et al., "Global Prevalence of Diabetes", Diabetes Care, vol. 27, No. 5, May 2004, pp. 1047-1053.
Wilkes, G. "Peripheral Neuropathy Related to Chemotherapy", Seminars in Oncology Nursing, 2007, vol. 23, 3. pp. 162-173.
Wilson, S. S G., "The heritability of antinociception: common pharmacogenetic mediation of five neurochemically distinct analgesics," *J Pharmacal Exp Ther*. 2003; 304 (2): 547-559.
Winkler, et al., "Synthesis of Highly Functionalized Furanones via Aldol Reaction of 3-Silyloxyfurans", Organic Letters, vol. 7, No. 3, pp. 387-389, 2005.
Wolf et al., Chemotherapy-induced peripheral neuropathy: Prevention and Treatment strategies, European Journal of Cancer, 2008, 44, 1507-1515.
Wolf, S., et al., "Chemotherapy-induced peripheral neuropathy: Prevention and treatment strategies," European Journal of Cancer, 2008, val. 44, issue 11, pp. 1507-1515.
Wong, H.Y., et al., Pentarnorphone for Management of Postoperative Pain. Anesth Analg. 1991; 72:656-60.
WU, et al., 37 Regulatory Perspectives of Type II Prodrug Development and Time- Dependent Toxicity Management: Nonclinical Pharm/Tox Analysis and the Role of Comparative Toxicology, Toxicology, 236: 1-6, 2007.
Wunsch, et al., Journal Med. Chem. vol. 55, No. 19, pp. 8209-8210, 2012.
Xiaoping, et al., "Involvement of the spinal NMDA receptor/PKCy signaling 12 pathway in the development of bone cancer pain", Brain Research, 2010, vol. 1335, pp. 83-90.
Xu, J. et al., 37 Identification of the PGRMCI protein complex as the putativP. sigma-2 receptor binding site. Nat Comnun. Jul. 5, 2011; 2:380.
Yaksh, T. L., Pharmacology of spinal adrenergic systems which modulate spinal nociceptive processing. *Pharmacal Biochem Behav*. 1985; 22(5): 845-58.
Yasuda, M., et al., "Mast Cell Stabilization Promotes Antinociceptive Effects in a Mouse Model of Postoperative Pain," J. Pain Res., 2013, vol. 6, pp. 161-166.
Yeretzian, et al., "Analysing the headspace of coffee by proton-transfer-reaction mass-spectrometry", Int J. Mass Spect, 223-224 (1-3), pp. 115-139, 2003.
Zahn, P.K., et al., "Mechanisms for Pain Caused by Incisions", Regional Anesthesia and Pain Medicine, 2002, vol. 271 No. 5, pp. 514-516.
Zhang et al. In Synapse 15(4):276-284 (1993), Abstract.
Zheng, F.Y., et al. "The Response of Spinal Microglia to Chemotherapy Evoked Painful Peripheral Neuropathies Is Distinct From That Evoked by Traumatic Nerve Injuries," *Neuroscience*, 2011, 176, pp. 447-454.
European Search Report dated Feb. 1, 2005 in connection with priorirty European Application No. EP 04077421.8.
European Search Report dated Sep. 12, 2008 in connection with European Application No. EP08384006.
European Search Report dated Oct. 2, 2008 in connection with European Application No. EP 08380122.
European Search Report dated Feb. 5, 2010 in connection with European Application No. EP09382144.
European Search Report dated Apr. 14, 2010 in connection with European Application No. EP09382261.
European Search Report dated Apr. 19, 2010 in connection with European Application No. EP10382024.7.
European Search Report dated Jun. 16, 2010 in connection with European Application No. EP 10382023.
European Search Report dated Jul. 1, 2010 in connection with European Patent Application No. EP10382025.
European Search Report dated Oct. 1, 2010 in connection with European Application No. EP10382215.1.
European Search report dated Oct. 22, 2010 by European Patent Office in connection with European Application No. EP 10 38 2148.
European Search Report dated Oct. 29, 2010 in connection with European Application No. EP10382136.
European Search Report dated Jan. 31, 2011 in connection with European Patent Application No. 10382326.6.
European Search Report dated Mar. 11, 2011 in connection with European Application No. EP10382330.8.
European Search Report dated Oct. 18, 2011 in connection with European Application No. EP11382157.3.
European Search Report dated May 3, 2013 in connection with European Patent Application No. EP13382140.
European Search Report dated Dec. 20, 2013 in connection with European Application No. EP13382246.0.
International Preliminary Report of Patentability with Written Opinion of the International Searching Authority dated Nov. 27, 2012 in connection with International Application No. PCT/EP2011/058633.
International Preliminary Report of Patentability with Written Opinion of the International Searching Authority dated Feb. 14, 2012 in connection with International Application No. PCT/EP2010/061720.
International Preliminary Report of Patentability with Written Opinion of the International Searching Authority dated May 30, 2012 in connection with International Application No. PCT/EP2010/068213.
International Preliminary Report of Patentability with Written Opinion of the International Searching Authority dated Feb. 12, 2013 in connection with International Patent Application No. PCT/EP2011/063583.
International Preliminary Report of Patentability with Written Opinion of the International Searching Authority dated Aug. 7, 2012 in connection with International Application No. PCT/EP11/51643.
International Preliminary Report of Patentability with Written Opinion of the International Searching Authority dated Mar. 15, 2016 in connection with International Applications No. PCT/EP2014/069370.
International Preliminary Report of Patentability with Written Opinion of the International Searching Authority dated Dec. 29, 2015 in connection with International Application No. PCT/EP2014/063360.
International Preliminary Report of Patentability with Written Opinion of the International Searching Authority dated Feb. 28, 2007 in connection with International Application No. PCT/EP2005/009375.
International Preliminary Report of Patentability with Written Opinion of the International Searching Authority dated Jun. 21, 2016 in connection with International Application No. PCT/EP2014/077996.
International Preliminary Report of Patentability with Written Opinion of the International Searching Authority dated Aug. 7, 2012 in connection with International Application No. PCT/EP2011/051644.
International Preliminary Report of Patentability with Written Opinion of the International Searching Authority dated Feb. 3, 2013 in connection with International Application No. PCT/EP2011/063286.
International Preliminary Report of Patentability with Written Opinion of the International Searching Authority dated Jun. 21, 2016 in connection with International Application No. PCT/EP2014/077992.
International Preliminary Report of Patentability with Written Opinion of the International Searching Authority dated Jun. 4, 2013 in connection with International Application No. PCT/EP2011/071584.

(56) References Cited

OTHER PUBLICATIONS

International Preliminary Report of Patentability with Written Opinion of the International Searching Authority dated Jun. 26, 2012 in connection with International Application No. PCT/EP2012/059232.
International Preliminary Report of Patentability with Written Opinion of the International Searching Authority dated May 30, 2012 in connection with International Application No. PCT/EP2010/068256.
International Preliminary Report of Patentability with Written Opinion of the International Searching Authority dated Nov. 27, 2012 in connection with International Applications No. PCT/EP2011/058224.
International Preliminary Report of Patentability with Written Opinion of the International Searching Authority dated Oct. 20, 2015 in connection with International Application No. PCT/EP2014/057608.
International Search report dated Jul. 7, 2009 in connection with International Application No. PCT/EP2009/001109.
International Preliminary Report of Patentability with Written Opinion of the International Searching Authority dated Oct. 26, 2010 in connection with International Application No. PCT/EP2009/054974.
International Preliminary Report of Patentability with Written Opinion of the International Searching Authority dated Oct. 26, 2010 in connection with International Application No. PCT/EP2009/054981.
International Search Report issued by the International Searching Authority dated Apr. 5, 2011 in connection with International Application No. PCT/EP2011/051644.
International Search Report dated Jan. 12, 2005 in connection with International Application No. PCT/EP2005/009375.
International Search Report dated Jun. 17, 2009 in connection with International Application No. PCT/EP2009/054974.
International Search report dated Oct. 31, 2014 in connection with International Application No. PCT/EP2014/069370.
International Search Report dated Jul. 24, 2009 in connection with International Application No. PCT/EP2009/054981.
International Search Report dated Nov. 25, 2010 in connection with International Application No. PCT/EP2010/061720.
International Search Report dated Mar. 8, 2011 in connection with International Applications No. PCT/EP2011/058224.
International Search Report dated Mar. 23, 2011 in connection with International Application No. PCT/EP2010/068213.
International Search Report dated May 4, 2011 in connection with International Application No. PCT/EP2011/051630.
International Search Report dated May 4, 2011 in connection with International Application No. PCT/EP2010/068256.
International Search report dated May 23, 2011 in connection with International Application No. PCT/EP11/51643.
International Search Report dated Aug. 31, 2011 in connection with International Application No. PCT/EP2011/063583.
International Search Report dated Sep. 21, 2011 in connection with International Application No. PCT/EP2011/058633.
International Search Report dated Jan. 16, 2012 in connection with International Application No. PCT/EP2001/071583.
International Search Report dated Jan. 31, 2012 in connection with International Application No. PCT/EP2011/063286.
International Search Report dated Mar. 13, 2012 in connection with International Application No. PCT/EP2011/071584.
International Search Report dated Jun. 26, 2012 in connection with International Application No. No. PCT/EP12/59232.
International Search Report dated Mar. 6, 2014 in connection with International Application No. PCT/EP2014/057608.
International Search report dated Sep. 17, 2014 in connection with International Application No. PCT/EP2014/063360.
Telleria-Diaz, et al., Pain, 2010, 148, pp. 26-35.
International Preliminary Report of Patentability with Written Opinion of the International Searching Authority dated Aug. 24, 2010 in connection with International Application No. PCT/EP2009/001109.
Ronsisvalle et al., "Opioid and sigma receptor studies. New development in the design of selective sigma ligands," Pure Appl. Chem. vol. 73, No. 9 pp. 1499-1509 (2001).
Office Action dated Mar. 18, 2013 in connection with Russian Patent Application No. 2010138634, filed Feb. 17, 2009.
Uchitel, O.D., et al., "Acute modulation of calcium currents and synaptic transmission by Gabapentinoids," Channels, 4:6, Nov./Dec. 2010, pp. 490-496.
Carter, Natalie, J., et al., "Duloxetine: a review of its use in the treatment of generalized anxiety disorder", CNS Drugs, 2009, vol. 23, No. 6, pp. 523-541.
Cobos, E.J., et al., "Pharmacology and therapeutic potential of sigma1 receptor ligands", Current Neuoropharmacology, 208, 6, pp. 344-366.
International Search Report for PCT/EP2014/077996 dated Jan. 30, 2015.
Kadiroglu, Ali, Kemal, et al., "The effect of venlafaxine HCl on painful peripheral diabetic neuropathy in patients with type 2 diabetes mellitus", Journal of Diabetes and Its Complications, 2008, 22, pp. 241-245.
Kunz, N.R., et al., "Diabetic neuropathic pain management with venlafaxine extended release", European Neuropsychopharmacology, 2000, P.6.014, pp. S389.
Marks, David, M., et al., "Serotonin-Norepinephrine reuptake inhibitors for pain control: Premise and promise", Current Neuropharmacology, 2009, 7, pp. 331-336.
Maurice, Tangui, et al., "The pharmacology of sigma-1 receptors", Pharmacology & Therapeutics, 2009, 124, pp. 195-206.
Merskey, IASP; Classification of Chronic Pain, 2nd Ed., IASP Press; 2002, pp. 210-213.
Reuben, Scott, S., et al., "Evaluation of efficacy of the perioperative administration of venlafaxine XR in the prevention of postmastectomy pain syndrome", Journal of Pain and Symptom Management, Feb. 2004, vol. 27, No. 2, pp. 133-139.
Romero, L., et al., "Pharmacological properties of S1RA, a new sigma-1 receptor antagonist that inhibits neuropathic pain and activity-induced spinal sensitization", British Journal of Pharmacology, 2012, 166, pp. 2289-2306.
Schreiber, Shaul, et al., "The antinociceptive effect of venlafaxine in mice is mediated through opioid and adrenergic mechanisma", Neuroscience Letters, 1999, 273, pp. 85-88.
Sussman, Norman, "SNRIs versus SSRIs: Mechanisms of action in treating depression and painful physical symptoms", Primary Care Companion J. Clin. Psychiatry, 2003, 5 (suppl 7), pp. 19-26.
Gonzalez-Cano, R. et al., "Sigma 1 Receptors are Involved in the Visceral Pain Induced by Intracolonic Administration of Capsaicin in Mice," Anesthesiology, Mar. 2013, vol. 118(3), pp. 691-700.

\* cited by examiner

SEROTONIN-NOREPINEPHRINE REUPTAKE INHIBITORS (SNRIS) AND SIGMA RECEPTOR LIGANDS COMBINATIONS

FIELD OF THE INVENTION

The present invention relates to an active substance combination, pharmaceutical compositions containing it and their use in medicine, particularly for the prophylaxis and/or treatment of pain.

BACKGROUND

The treatment of pain conditions is of great importance in medicine. There is currently a world-wide need for additional pain therapy. The pressing requirement for a specific treatment of pain conditions is documented in the large number of scientific works that have appeared recently in the field of applied analgesics.

PAIN is defined by the International Association for the Study of Pain (IASP) as "an unpleasant sensory and emotional experience associated with actual or potential tissue damage, or described in terms of such damage" (IASP, Classification of chronic pain, 2nd Edition, IASP Press (2002), 210). Although it is a complex process influenced by both physiological and psychological factors and is always subjective, its causes or syndromes can be classified. Pain can be classified based on temporal, aetiological or physiological criteria. When pain is classified by time, it can be acute or chronic. Aetiological classifications of pain are malignant or non-malignant. A third classification is physiological, which includes nociceptive pain (results from detection by specialized transducers in tissues attached to A-delta and C-fibers), that can be divided into somatic and visceral types of pain, and neuropathic pain (results from irritation or damage to the nervous system), that can be divided into peripheral and central neuropathic pain. Pain is a normal physiological reaction of the somatosensory system to noxious stimulation which alerts the individual to actual or potential tissue damage. It serves a protective function of informing us of injury or disease, and usually remits when healing is complete or the condition is cured. However, pain may result from a pathological state characterized by one or more of the following: pain in the absence of a noxious stimulus (spontaneous pain), increased duration of response to brief stimulation (ongoing pain or hyperpathia), reduced pain threshold (allodynia), increased responsiveness to suprathreshold stimulation (hyperalgesia), spread of pain and hyperalgesia to uninjured tissue (referred pain and secondary hyperalgesia), and abnormal sensations (e.g., dysesthesia, paresthesia).

Serotonin-Norepinephrine Reuptake Inhibitors (SNRIs) are a class of antidepressant drugs used in the treatment of major depression and other mood disorders that increase the levels of both serotonin and norepinephrine by inhibiting their reabsorption (reuptake) into cells in the CNS (Central Nervous System). There have been numerous studies demonstrating the analgesic effect of antidepressants, providing evidence that antidepressants are beneficial in the treatment of so-called 'chronic pain'. The precise mechanisms involved in the pathogenesis of persistent pain states are not fully understood, but there is growing recognition that the disinhibition and imbalance of serotonin and norepinephrine in endogenous pain inhibitory pathways may contribute to persistent pain (Sussman, 2003; Marks et al., 2009).

Venlafaxine is the first and most commonly used SNRI. It was introduced by Wyeth in 1994. The reuptake effects of venlafaxine are dose-dependent. At low doses it acts only on serotonergic transmission, at moderate doses it acts on serotonergic and noradrenergic systems, whereas at high doses, it can also affect dopaminergic neurotransmission (Marks et al., 2009). Desvenlafaxine, Duloxetine, Milnacipram, Levomilnacipram, Sibutramine or Bicifadine are other known SNRIs, besides Venlafaxine.

Clinical indications of SNRIs include major depressive disorder (MDD), generalized anxiety disorder (GAD), social anxiety disorder (SAD), panic disorder, neuropathic pain, fibromyalgia and chronical musculoskeletal pain.

There have been reported a number of side effects associated with SNRIs. The most common include loss of appetite, weight, and sleep. There may also be drowsiness, dizziness, fatigue, headache, increase in suicidal thoughts, emesis, nausea/vomiting, sexual dysfunction [including diminished interest in sex (libido) and difficulty reaching climax (anorgasmia)], and urinary retention. Elevation of norepinephrine levels can sometimes cause anxiety, mildly elevated pulse, and elevated blood pressure. People at risk for hypertension and heart disease should have their blood pressure monitored. Thus therapeutic utility of SNRIs is limited by undesirable adverse effects.

Two subtypes of Sigma receptors (Sigma-1 and Sigma-2 receptors) have been identified (Cobos et al., 2008). Confused with opioid receptors for many years due to the cross-reactivity of some ligands, the Sigma-1 receptor is a 24-kDa molecular mass protein of 223 amino acids anchored to the endoplasmic reticulum and plasma membranes (Cobos et al., 2008; Maurice and Su, 2009). Sigma-1 receptor is a unique ligand-regulated molecular chaperone which is activated under stress or pathological conditions and interacts with several neurotransmitter receptors and ion channels to modulate their function. The effects reported preclinically with Sigma-1 receptor ligands are consistent with a role for Sigma-1 receptor in central sensitization and pain hypersensitivity and suggest a potential therapeutic use of Sigma-1 receptor antagonists for the management of neuropathic pain as monotherapy (Romero et al., 2012).

Pyrazole derivatives of general formula (I) according to the present invention are described in WO 2006/021462 as compounds having pharmacological activity towards the sigma (σ) receptor useful, inter alia, in the prophylaxis and/or treatment of pain.

Pharmaceutical compositions (WO 2011/064296 A1), salts (WO 2011/064315 A1), polymorphs and solvates (WO 2011/095579 A1), and other solid forms (WO 2012/019984 A1) of said sigma ligands of formula (I) have been also disclosed as well as combinations with other active substances such a with opioids or opiates (WO 2009/130310 A1, WO 2012/016980 A2, WO 2012/072782 A1) or with chemotherapeutic drugs (WO 2011/018487 A1, WO 2011/144721 A1).

As mentioned above, therapeutic utility of SNRIs is limited by undesirable adverse effects including cardiovascular and gastrointestinal toxicity. Thus, strategies aimed to reduce doses needed for SNRIs indications, especially for analgesia, are desirable in order to improve their therapeutic window and extend their use in clinics.

BRIEF DESCRIPTION OF THE INVENTION

It is an object of the present invention to provide a medicament suitable for the prophylaxis and/or treatment of pain, which preferably does not show the undesired side effects of the SNRIs when used for the prophylaxis and/or treatment of pain, or at least less frequent and/or less pronounced.

The inventors of the present invention have found and demonstrated that the administration of some specific Sigma receptor ligands in conjunction with SNRIs surprisingly potentiates synergistically the analgesia.

In particular, the inventors of the present invention have found and demonstrated that the administration of some specific Sigma receptor ligands in conjunction with SNRIs potentiates synergistically the analgesic effect of the latter, indicating that the combination of a Sigma ligand and a SNRI reduces the doses of the latter needed to obtain effective analgesia.

Likewise, the inventors of the present invention have found and demonstrated that the administration of some specific Sigma receptor ligands in conjunction with SNRIs potentiates synergistically the analgesic effect of Sigma ligands.

Therefore, one aspect of the present invention relates to a synergistic combination comprising at least one Serotonin-Norepinephrine Reuptake Inhibitor (SNRI) and at least one Sigma ligand of general formula (I)

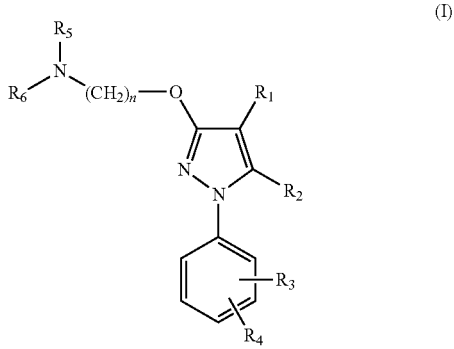

wherein,

R$_1$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

R$_2$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

R$_3$ and R$_4$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen, or together with the phenyl they form an optionally substituted fused ring system;

R$_5$ and R$_6$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

or together form, with the nitrogen atom to which they are attached, a substituted or unsubstituted, aromatic or non-aromatic heterocyclyl group;

n is selected from 1, 2, 3, 4, 5, 6, 7 and 8;

t is 0, 1 or 2;

R$_8$ and R$_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted, aromatic or non-aromatic heterocyclyl, substituted or unsubstituted alkoxy, substituted or unsubstituted aryloxy, and halogen, or a pharmaceutically acceptable salt, isomer, prodrug or solvate thereof.

More preferably, the Sigma ligands according to the present invention are selective Sigma-1 antagonist receptor ligands of above defined general formula (I) or a pharmaceutically acceptable salt, isomer, prodrug or solvate thereof.

Another aspect of this invention refers to the synergistic combination comprising at least one Sigma ligand of general formula (I) as defined above, or a pharmaceutically acceptable salt, isomer, prodrug or solvate thereof, and at least one SNRI for use in medicine.

Another aspect of this invention refers to the synergistic combination comprising at least one Sigma ligand of general formula (I) as defined above, or a pharmaceutically acceptable salt, isomer, prodrug or solvate thereof, and at least one SNRI for use in the prophylaxis and/or treatment of pain.

Another aspect of this invention refers to the use of the synergistic combination comprising at least one Sigma ligand of general formula (I) as defined above, or a pharmaceutically acceptable salt, isomer, prodrug or solvate thereof, and at least one SNRI for manufacturing a medicament for the prophylaxis and/or treatment of pain.

Another aspect of the invention is a method of treatment and/or prophylaxis of a patient suffering from pain, or likely to suffer pain, the method comprising administering to the patient in need of such a treatment or prophylaxis a therapeutically effective amount of a synergistic combination comprising at least one Sigma ligand of general formula (I) as defined above, or a pharmaceutically acceptable salt, isomer, prodrug or solvate thereof, and at least one SNRI.

Another aspect of this invention refers to the synergistic combination comprising at least one Sigma ligand of general formula (I) as defined above, or a pharmaceutically acceptable salt, isomer, prodrug or solvate thereof, and at least one SNRI for use in the prophylaxis and/or treatment of pain by potentiating the analgesic effect of the SNRI.

Another aspect of this invention refers to the use of the synergistic combination comprising at least one Sigma ligand of general formula (I) as defined above, or a pharmaceutically acceptable salt, isomer, prodrug or solvate thereof, and at least one SNRI for manufacturing a medicament for the prophylaxis and/or treatment of pain by potentiating the analgesic effect of the SNRI.

Another aspect of this invention refers to the use of Sigma ligands of general formula (I) for potentiating the analgesic effect of SNRIs.

The pharmaceutical synergistic combination of the invention may be formulated for its simultaneous, separate or sequential administration.

These aspects and preferred embodiments thereof are additionally also defined hereinafter in the detailed description, as well as in the claims.

DETAILED DESCRIPTION OF THE INVENTION

Figure 1:
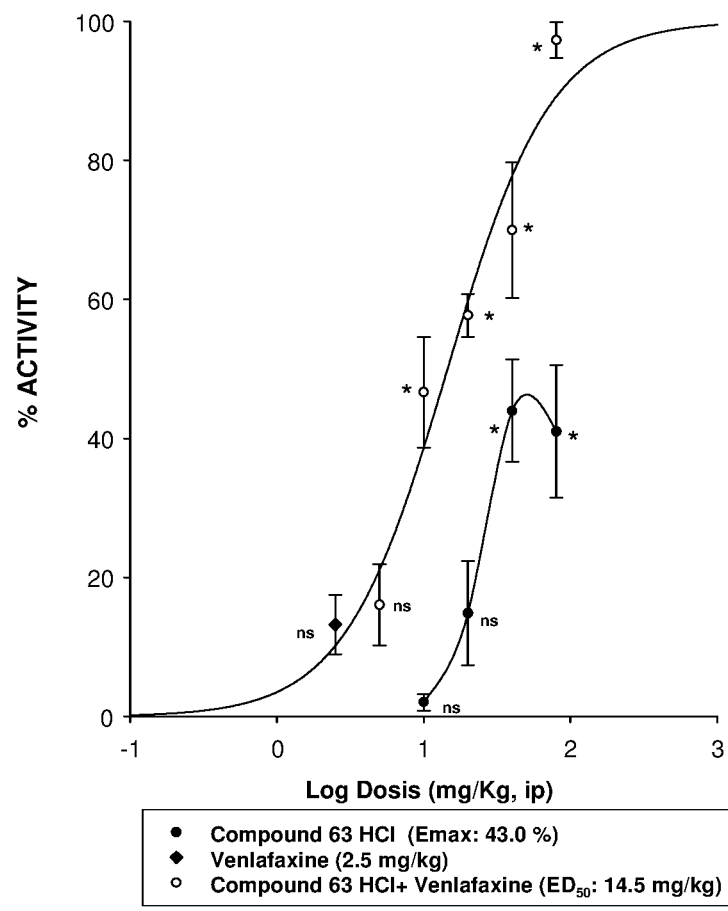
FIG. 1: Potentiation of venlafaxine analgesia (2.5 mg/kg) by compound 63.HCl (5, 10, 20, 40 and 80 mg/kg) in the mechanical allodynia of the post-operative pain model in rats. n=10, *: p<0.05; ns: p>0.05 Dunnett, compound 63.HCl+Venlafaxine vs. Venlafaxine.

The efficacy of the active components can sometimes be improved by addition of other (active) ingredients. More rarely, the observed efficacy of the combination of ingredients can be significantly higher than what would be expected from the amounts of the individual ingredients used, thus indicating potentiation of the activity of the components of the combination.

The present inventors have found that Sigma receptor ligands of general formula (I) are able to potentiate the analgesic effect of SNRIs.

In the context of the present invention, the following terms have the meaning detailed below.

"Alkyl" refers to a straight or branched hydrocarbon chain radical containing no unsaturation, and which is attached to the rest of the molecule by a single bond. Typical alkyl groups have from 1 to about 12, 1 to about 8, or 1 to about 6 carbon atoms, e.g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, heterocyclyl, amino, nitro, mercapto, alkylthio, etc. If substituted by aryl, it corresponds to an "arylalkyl" radical, such as benzyl or phenethyl. If substituted by heterocyclyl, it corresponds to a "heterocyclylalkyl" radical.

"Alkenyl" refers to a straight or branched hydrocarbon chain radical containing at least two carbon atoms and at least one unsaturation, and which is attached to the rest of the molecule by a single bond. Typical alkenyl radicals have from 2 to about 12, 2 to about 8 or 2 to about 6 carbon atoms. In a particular embodiment, the alkenyl group is vinyl, 1-methyl-ethenyl, 1-propenyl, 2-propenyl, or butenyl.

"Alkynyl" refers to a straight or branched hydrocarbon chain radical containing at least two carbon atoms and at least one carbon-carbon triple bond, and which is attached to the rest of the molecule by a single bond. Typical alkynyl radicals have from 2 to about 12, 2 to about 8 or 2 to about 6 carbon atoms. In a particular embodiment, the alkynyl group is ethynyl, propynyl (e.g. 1-propynyl, 2-propynyl), or butynyl (e.g. 1-butynyl, 2-butynyl, 3-butynyl).

"Cycloalkyl" refers to an alicyclic hydrocarbon which is saturated or partially saturated. Typical cycloalkyl radicals contain from 1 to 3 separated and/or fused rings and from 3 to about 18 carbon atoms, preferably from 3 to 10 carbon atoms, such as cyclopropyl, cyclohexyl or adamantyl. In a particular embodiment, the cycloalkyl radical contains from 3 to about 6 carbon atoms.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl (e.g. 2-naphthyl), indenyl, fenanthryl or anthracyl radical.

"Heterocyclyl" includes both aromatic and non-aromatic heterocyclic groups.

"Aromatic Heterocyclyl" or "Heteroaryl" refers to heteroaromatic groups containing from 1 to 3 separated and/or fused rings and from 3 to about 18 ring atoms. Preferably heteroaromatic groups contain from 5 to about 10 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothienyl, benzothiazolyl, benzoxazolyl, quinazolinyl, quinoxalinyl, naphthyridinyl, and furopyridinyl.

"Non-aromatic Heterocyclyl" refers to heteroalicyclic groups containing from 1 to 3 separated and/or fused rings and from 3 to about 18 ring atoms. Preferably heteroalicyclic groups contain from 5 to about 10 ring atoms. Suitable heteroalicyclic groups in the compounds of the present invention contain one, two or three heteroatoms selected from N, O or S atoms and include, e.g., pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, oxetanyl, thietanyl, homopiperidinyl, oxepanyl, thiepanyl, azepinyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

"Alkoxy" refers to a radical of the formula —OR$_a$ where R$_a$ is an alkyl radical as defined above having one or more (e.g., 1, 2, 3 or 4) oxygen linkages and typically from 1 to about 12, 1 to about 8 or 1 to about 6 carbon atoms, e.g., methoxy, ethoxy, propoxy, etc.

"Aryloxy" refers to a radical of formula —O-aryl, where aryl is as previously defined. Some examples of aryloxy compounds are —O-phenyl (i.e. phenoxy), —O-p-tolyl, —O-m-tolyl, —O-o-tolyl or —O-naphthyl.

"Amino" refers to a radical of the formula —NH$_2$, —NHR$_a$ or —NR$_a$R$_b$, optionally quaternized. In an embodiment of the invention each of R$_a$ and R$_b$ is independently selected from hydrogen and an alkyl radical as defined above. Therefore, examples of amino groups are, methylamino, ethylamino, dimethylamino, diethylamino, propylamino, etc. . . .

"Halogen", "halo" or "hal" refers to bromo, chloro, iodo or fluoro.

"Fused ring system" refers to a polycyclic ring system that contains fused rings. Typically, the fused ring system contains 2 or 3 rings and/or up to 18 ring atoms. As defined above, cycloalkyl radicals, aryl radicals and heterocyclyl radicals may form fused ring systems. Thus, fused ring system may be aromatic, partially aromatic or not aromatic and may contain heteroatoms. A spiro ring system is not a fused-polycyclic by this definition, but fused polycyclic ring systems of the invention may themselves have spiro rings attached thereto via a single ring atom of the system. Examples of fused ring systems are, but are not limited to, adamantyl, naphthyl (e.g. 2-naphthyl), indenyl, fenanthryl, anthracyl, pyrenyl, benzimidazole, benzothiazole, etc.

Unless otherwise stated specifically in the specification, all the groups may be optionally substituted, if applicable. References herein to substituted groups in the compounds of the present invention refer to the specified moiety that may be substituted at one or more (e.g., 1, 2, 3 or 4) available positions by one or more suitable groups, e.g., halogen such as fluoro, chloro, bromo and iodo; cyano; hydroxyl; nitro; azido; acyl, such as alkanoyl, e.g. a $C_{1-6}$ alkanoyl group, and the like; carboxamido; alkyl groups including those groups having 1 to about 12 carbon atoms or from 1 to about 6 carbon atoms and more preferably 1-3 carbon atoms; alkenyl and alkynyl groups including groups having one or more (e.g., 1, 2, 3 or 4) unsaturated linkages and from 2 to about 12 carbon or from 2 to about 6 carbon atoms; alkoxy groups having one or more (e.g., 1, 2, 3 or 4) oxygen linkages and from 1 to about 12 carbon atoms or 1 to about 6 carbon atoms; aryloxy such as phenoxy; alkylthio groups including those moieties having one or more (e.g., 1, 2, 3 or 4) thioether linkages and from 1 to about 12 carbon atoms or from 1 to about 6 carbon atoms; alkylsulfinyl groups including those moieties having one or more (e.g., 1, 2, 3 or 4) sulfinyl linkages and from 1 to about 12 carbon atoms or from 1 to about 6 carbon atoms; alkylsulfonyl groups including those moieties having one or more (e.g., 1, 2, 3 or 4) sulfonyl linkages and from 1 to about 12 carbon atoms or from 1 to about 6 carbon atoms; aminoalkyl groups such as groups having one or more (e.g., 1, 2, 3 or 4) N atoms and from 1 to about 12 carbon atoms or from 1 to about 6 carbon atoms; carbocylic aryl having 6 or more carbons, particularly phenyl or naphthyl and aralkyl such as benzyl.

The term "salt" must be understood as any form of a compound used in accordance with this invention in which said compound is in ionic form or is charged and coupled to a counter-ion (a cation or anion) or is in solution. This definition also includes quaternary ammonium salts and complexes of the molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention normally an acid (deprotonated) such as an anion and at least one physiologically tolerated cation, preferably inorganic, particularly when used on humans and/or mammals. Salts with alkali and alkali earth metals are preferred particularly, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention normally protonated, for example in nitrogen such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of a compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of a compound referred to herein is also within the scope of the invention. The term "prodrug" is used in its broadest sense and encompasses those derivatives that are converted in vivo to the compounds of the invention. Examples of prodrugs include, but are not limited to, derivatives of the compounds referred to herein such as compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described in "Burger's Medicinal Chemistry, Drug Discovery and Development" 7th ed. (Donald J. Abraham ed., 2010, Wiley), "Design of Prodrugs" (H. Bundgaard ed., 1985, Elsevier), "A Textbook of Drug Design and Development" (P. Krogsgaard-Larsen and H. Bundgaard eds., 1991, Harwood Academic Publishers; Chapter 5: "Design and Applications of Prodrugs", p. 113-191) and "Textbook of Drug Design and Discovery" 4th ed. (P. Krogsgaard-Larsen et al. ed., 2010, Taylor & Francis).

Any compound referred to herein is intended to represent such specific compound as well as certain variations or forms. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of the invention or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrug.

As used herein, the terms "treat", "treating" and "treatment" include the eradication, removal, reversion, alleviation, modification, or control of pain after its onset.

As used herein, the terms "prevention", "preventing", "preventive" "prevent" and "prophylaxis" refer to the capacity of a therapeutic to avoid, minimize or difficult the onset or development of a disease or condition before its onset, in this case pain.

Therefore, by "treating" or "treatment" and/or "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as pain. As such, the method of the present invention also includes situations where the condition is completely inhibited, e.g., prevented from happening, or stopped, e.g., terminated, such that the subject no longer experiences the condition. As such, the present method includes both preventing and managing pain, particularly, peripheral neuropathic pain, central neuropathic pain, allodynia, causalgia, hyperalgesia, hyperesthesia, hyperpathia, neuralgia, neuritis or neuropathy.

As used herein, the term "potentiating the analgesic effect of a SNRI" refers to the increase in the effectiveness of the analgesic effect of said SNRI produced by sigma ligands. In an embodiment of the invention, said potentiating effect induces an increase in the analgesic effect of the SNRI by a factor of 1.2, 1.5, 2, 3, 4 or more when compared with the SNRI when administered in isolation. The measurement can be done following any known method in the art.

As used herein, the term "potentiating the analgesic effect of a Sigma ligand" refers to the increase in the effectiveness of the analgesic effect of said Sigma ligand produced by SNRI. In an embodiment of the invention said potentiating effect induces an increase in the analgesic effect of the Sigma ligand by a factor of 1.2, 1.5, 2, 3, 4 or more when compared with the Sigma ligand when administered in isolation. The measurement can be done following any known method in the art.

As above mentioned, the Sigma ligands of general formula (I) surprisingly potentiate the analgesic effect of SNRIs, thus reducing the doses needed to obtain effective analgesia of the latter. In preferred variants, the synergistic combination of the invention comprises at least one Serotonin-Norepinephrine Reuptake Inhibitor (SNRI) and at least one Sigma ligand of general formula (I), said SNRI being present in the combination in a subactive dose or in a non-effective amount (that is, in a dose or amount that is not active or effective to provide the desired effect when used alone).

"Synergy" may be defined as the interaction of multiple elements in a system to produce an effect different from or greater than the sum of their individual effects. Thus, the combinations of the present invention are synergistic.

In a preferred embodiment, $R_1$ in the compounds of general formula (I) is selected from H, —COR$_8$, and substituted or unsubstituted alkyl. More preferably, $R_1$ is selected from H, methyl and acetyl. A more preferred embodiment is when $R_1$ is H.

In another preferred embodiment, $R_2$ in the compounds of formula (I) represents H or substituted or unsubstituted alkyl, more preferably methyl.

In a particular embodiment of the invention, $R_3$ and $R_4$ in the compounds of formula (I) are situated in the meta and para positions of the phenyl group, and preferably, they are selected independently from halogen and substituted or unsubstituted alkyl.

In an especially preferred embodiment of the invention, in the compounds of formula (I) both $R_3$ and $R_4$ together with the phenyl group form an optionally substituted fused ring system. More preferably, said fused ring system is selected from a substituted or unsubstituted fused aryl group and a substituted or unsubstituted aromatic or partially aromatic fused heterocyclyl group. Said fused ring system preferably contains two rings and/or from 9 to about 18 ring atoms, more preferably 9 or 10 ring atoms. Even more preferably, the fused ring system is naphthyl, especially a 2-naphthyl ring system, substituted or unsubstituted.

Also in the compounds of formula (I), embodiments where n is selected from 2, 3 or 4 are preferred in the context of the present invention, more preferably n is 2.

In another embodiment it is preferred in the compounds of formula (I) that $R_5$ and $R_6$ are, each independently, $C_{1-8}$alkyl, or together with the nitrogen atom to which they are attached form a substituted or unsubstituted heterocyclyl group, in particular a group chosen among morpholinyl, piperidinyl, and pyrrolidinyl group. More preferably, $R_5$ and $R_6$ together form a morpholine-4-yl group.

In additional preferred embodiments, the preferences described above for the different substituents are combined. The present invention is also directed to such combinations of preferred substitutions in the formula (I) above.

In preferred variants of the invention, the Sigma ligand of general formula (I) is selected from:

[1] 4-{2-(1-(3,4-dichlorophenyl)-5-methyl-1H pyrazol-3-yloxy)ethyl}morpholine,

[2] 2-[1-(3,4-Dichlorophenyl)-5-methyl-1H-pyrazol-3-yloxy]-N,N-diethylethanamine,

[3] 1-(3,4-Dichlorophenyl)-5-methyl-3-[2-(pyrrolidin-1-yl)ethoxy]-1H-pyrazole,

[4] 1-(3,4-Dichlorophenyl)-5-methyl-3-[3-(pyrrolidin-1-yl)propoxy]-1H-pyrazole,
[5] 1-{2-[1-(3,4-Dichlorophenyl)-5-methyl-1H-pyrazol-3-yloxy]ethyl}piperidine,
[6] 1-{2-[1-(3,4-dichlorophenyl)-5-methyl-1H-pyrazol-3-yloxy]ethyl}-1H-imidazole,
[7] 3-{1-[2-(1-(3,4-Dichlorophenyl)-5-methyl-1H-pyrazol-3-yloxy)ethyl]piperidin-4-yl}-3H-imidazo[4,5-b]pyridine,
[8] 1-{2-[1-(3,4-Dichlorophenyl)-5-methyl-1H-pyrazol-3-yloxy]ethyl}-4-methylpiperazine,
[9] Ethyl 4-{2-[1-(3,4-dichlorophenyl)-5-methyl-1H-pyrazol-3-yloxy]ethyl}piperazine carboxylate,
[10] 1-(4-(2-(1-(3,4-dichlorophenyl)-5-methyl-1H-pyrazol-3-yloxy)ethyl)piperazin-1-yl)ethanone,
[11] 4-{2-[1-(4-Methoxyphenyl)-5-methyl-1H-pyrazol-3-yloxy]ethyl}morpholine,
[12] 1-(4-Methoxyphenyl)-5-methyl-3-[2-(pyrrolidin-1-yl)ethoxy]-1H-pyrazole,
[13] 1-(4-Methoxyphenyl)-5-methyl-3-[3-(pyrrolidin-1-yl)propoxy]-1H-pyrazole,
[14] 1-[2-(1-(4-Methoxyphenyl)-5-methyl-1H-pyrazol-3-yloxy)ethyl]piperidine,
[15] 1-{2-[1-(4-Methoxyphenyl)-5-methyl-1H-pyrazol-3-yloxy]ethyl}-1H-imidazole,
[16] 4-{2-[1-(3,4-Dichlorophenyl)-5-phenyl-1H-pyrazol-3-yloxy]ethyl}morpholine,
[17] 1-(3,4-Dichlorophenyl)-5-phenyl-3-[2-(pyrrolidin-1-yl)ethoxy]-1H-pyrazole,
[18] 1-(3,4-Dichlorophenyl)-5-phenyl-3-[3-(pyrrolidin-1-yl)propoxy]-1H-pyrazole,
[19] 1-{2-[1-(3,4-Dichlorophenyl)-5-phenyl-1H-pyrazol-3-yloxy]ethyl}piperidine,
[20] 1-{2-[1-(3,4-Dichlorophenyl)-5-phenyl-1H-pyrazol-3-yloxy]ethyl}-1H-imidazole,
[21] 2-{2-[1-(3,4-dichlorophenyl)-5-phenyl-1H-pyrazol-3-yloxy]ethyl}-1,2,3,4-tetrahydroisoquinoline,
[22] 4-{4-[1-(3,4-Dichlorophenyl)-5-methyl-1H-pyrazol-3-yloxy]butyl}morpholine,
[23] 1-(3,4-Dichlorophenyl)-5-methyl-3-[4-(pyrrolidin-1-yl)butoxy]-1H-pyrazole,
[24] 1-{4-[1-(3,4-Dichlorophenyl)-5-methyl-1H-pyrazol-3-yloxy]butyl}piperidine,
[25] 1-{4-[1-(3,4-Dichlorophenyl)-5-methyl-1H-pyrazol-3-yloxy]butyl}-4-methylpiperazine,
[26] 1-{4-[1-(3,4-Dichlorophenyl)-5-methyl-1H-pyrazol-3-yloxy]butyl}-1H-imidazole,
[27] 4-[1-(3,4-Dichlorophenyl)-5-methyl-1H-pyrazol-3-yloxy]-N,N-diethylbutan-1-amine,
[28] 1-{4-[1-(3,4-dichlorophenyl)-5-methyl-1H-pyrazol-3-yloxy]butyl}-4-phenylpiperidine,
[29] 1-{4-[1-(3,4-dichlorophenyl)-5-methyl-1H-pyrazol-3-yloxy]butyl}-6,7-dihydro-1H-indol-4(5H)-one,
[30] 2-{4-[1-(3,4-dichlorophenyl)-5-methyl-1H-pyrazol-3-yloxy]butyl}-1,2,3,4-tetrahydroisoquinoline,
[31] 4-{2-[1-(3,4-dichlorophenyl)-5-isopropyl-1H-pyrazol-3-yloxy]ethyl}morpholine,
[32] 2-[1-(3,4-Dichlorophenyl)-5-isopropyl-1H-pyrazol-3-yloxy]-N,N-diethylethanamine,
[33] 1-(3,4-Dichlorophenyl)-5-isopropyl-3-[2-(pyrrolidin-1-yl)ethoxy]-1H-pyrazole,
[34] 1-(3,4-Dichlorophenyl)-5-isopropyl-3-[3-(pyrrolidin-1-yl)propoxy]-1H-pyrazole,
[35] 1-{2-[1-(3,4-Dichlorophenyl)-5-isopropyl-1H-pyrazol-3-yloxy]ethyl}piperidine,
[36] 2-{2-[1-(3,4-dichlorophenyl)-5-isopropyl-1H-pyrazol-3-yloxy]ethyl}-1,2,3,4-tetrahydroisoquinoline,
[37] 4-{2-[1-(3,4-dichlorophenyl)-1H-pyrazol-3-yloxy]ethyl}morpholine,
[38] 2-[1-(3,4-dichlorophenyl)-1H-pyrazol-3-yloxy] N,N-diethylethanamine,
[39] 1-(3,4-dichlorophenyl)-3-[2-(pyrrolidin-1-yl)ethoxy]-1H-pyrazole,
[40] 1-{2-[1-(3,4-dichlorophenyl)-1H-pyrazol-3-yloxy]ethyl}piperidine,
[41] 1-(3,4-dichlorophenyl)-3-[3-(pyrrolidin-1-yl)propoxy]-1H-pyrazole,
[42] 1-{2-[1-(3,4-Dichlorophenyl)-5-methyl-1H-pyrazol-3-yloxy]ethyl}piperazine,
[43] 1-{2-[1-(3,4-Dichlorophenyl)-5-methyl-1H-pyrazol-3-yloxy]ethyl}pyrrolidin-3-amine,
[44] 4-{2-[1-(3,4-Dichlorophenyl)-4,5-dimethyl-1H-pyrazol-3-yloxy]ethyl}morpholine,
[46] 2-[1-(3,4-Dichlorophenyl)-4,5-dimethyl-1H-pyrazol-3-yloxy]-N,N-diethylethanamine,
[47] 1-(3,4-Dichlorophenyl)-4,5-dimethyl-3-[2-(pyrrolidin-1-Methoxy]-1H-pyrazole,
[48] 1-(3,4-Dichlorophenyl)-4,5-dimethyl-3-[3-(pyrrolidin-1-yl)propoxy]-1H-pyrazole,
[49] 1-{2-[1-(3,4-Dichlorophenyl)-4,5-dimethyl-1H-pyrazol-3-yloxy]ethyl}piperidine,
[50] 4-{4-[1-(3,4-dichlorophenyl)-1H-pyrazol-3-yloxy]butyl}morpholine,
[51] (2S,6R)-4-{4-[1-(3,4-dichlorophenyl)-1H-pyrazol-3-yloxy]butyl}-2,6-dimethylmorpholine,
[52] 1-{4-[1-(3,4-Dichlorophenyl)-1H-pyrazol-3-yloxy]butyl}piperidine,
[53] 1-(3,4-Dichlorophenyl)-3-[4-(pyrrolidin-1-yl)butoxy]-1H-pyrazole,
[55] 4-[1-(3,4-dichlorophenyl)-1H-pyrazol-3-yloxy]-N,N-diethylbutan-1-amine,
[56] N-benzyl-4-[1-(3,4-dichlorophenyl)-1H-pyrazol-3-yloxy]-N-methylbutan-1-amine,
[57] 4-[1-(3,4-dichlorophenyl)-1H-pyrazol-3-yloxy]-N-(2-methoxyethyl)-N-methylbutan-1-amine,
[58] 4-{4-[1-(3,4-dichlorophenyl)-1H-pyrazol-3-yloxy]butyl}thiomorpholine,
[59] 1-[1-(3,4-Dichlorophenyl)-5-methyl-3-(2-morpholinoethoxy)-1H-pyrazol-4-yl]ethanone,
[60] 1-{1-(3,4-dichlorophenyl)-5-methyl-3-[2-(pyrrolidin-1-Methoxy]-1H-pyrazol-4-yl}ethanone,
[61] 1-{1-(3,4-dichlorophenyl)-5-methyl-3-[2-(piperidin-1-yl)ethoxy]-1H-pyrazol-4-yl}ethanone,
[62] 1-{1-(3,4-dichlorophenyl)-3-[2-(diethylamino)ethoxy]-5-methyl-1H-pyrazol-4-yl}ethanone,
[63] 4-{2-[5-Methyl-1-(naphthalen-2-yl)-1H-pyrazol-3-yloxy]ethyl}morpholine,
[64] N,N-Diethyl-2-[5-methyl-1-(naphthalen-2-yl)-1H-pyrazol-3-yloxy] ethanamine,
[65] 1-{2-[5-Methyl-1-(naphthalen-2-yl)-1H-pyrazol-3-yloxy]ethyl}piperidine, and
[66] 5-Methyl-1-(naphthalen-2-yl)-3-[2-(pyrrolidin-1-yl)ethoxy]-1H-pyrazole,
or a pharmaceutically acceptable salt, isomer, solvate or prodrug thereof.

In a preferred variant of the invention, the Sigma ligand of general formula (I) is 4-{2-[5-Methyl-1-(naphthalen-2-yl)-1H-pyrazol-3-yloxy]ethyl}morpholine or a salt thereof.

Preferably, the compound of general formula (I) used is 4-{2-[5-Methyl-1-(naphthalen-2-yl)-1H-pyrazol-3-yloxy]ethyl}morpholine hydrochloride.

These particular compounds are designated in the examples of the present invention as compound 63 and compound 63.HCl.

The compounds of general formula (I) and their salts or solvates can be prepared as disclosed in the previous application WO2006/021462.

By "SNRI" is meant any member of the class of compounds that act upon, and increase, the levels of two neurotransmitters in the brain known to play an important part in mood: serotonin, and norepinephrine.

Examples of Serotonin-Norepinephrine Reuptake Inhibitors (SNRIs) in the present invention include, but are not limited to, venlafaxine, desvenlafaxine, duloxetine, milnacipram, levomilnacipram, sibutramine, nefazodone and bicifadine or a pharmaceutically acceptable salt, isomer, prodrug or solvate thereof. Particular salts are the following: venlafaxine hydrochloride, desvenlafaxine succinate monohydrate, duloxetine hydrochloride, sibutramine hydrochloride monohydrate, sibutramine mesylate hemihydrate and nefazodone hydrochloride.

Structural analogs of the above-mentioned SNRIs are also contemplated by the present invention. US 2007/0208134 discloses several examples of these analogs, which can be synthesized by conventional procedures such as the methods described in the references cited therein.

Structural analogs of venlafaxine are those compounds having the formula:

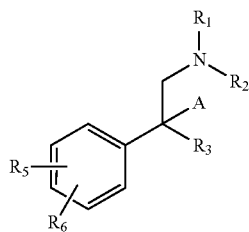

as well as pharmaceutically acceptable salts thereof, wherein A is a moiety of the formula:

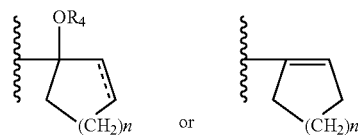

where the dotted line represents optional unsaturation; $R_1$ is hydrogen or alkyl; $R_2$ is $C_{1-4}$ alkyl; $R_4$ is hydrogen, $C_{1-4}$ alkyl, formyl or alkanoyl; $R_3$ is hydrogen or $C_{1-4}$ alkyl; $R_5$ and $R_6$ are, independently, hydrogen, hydroxyl, $C_{1-4}$ alkyl, $C_{1-4}$ alkoxy, $C_{1-4}$ alkanoyloxy, cyano, nitro, alkylmercapto, amino, $C_{1-4}$ alkylamino, dialkylamino, $C_{1-4}$ alkanamido, halo, trifluoromethyl or, taken together, methylenedioxy; and n is 0, 1, 2, 3 or 4.

Structural analogs of duloxetine are those having the formula:

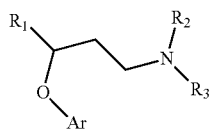

as well as pharmaceutically acceptable salts thereof, wherein $R_1$ is $C_5$-$C_7$ cycloalkyl, thienyl, halothienyl, ($C_1$-$C_4$alkyl)thienyl, furanyl, pyridyl, or thiazolyl; each of $R_2$ and $R_3$ Ar is, independently, hydrogen or methyl; Ar is

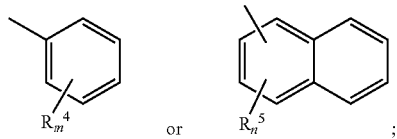

each $R_4$ is, independently, halo, $C_1$-$C_4$ alkyl, $C_1$-$C_3$ alkoxy, or trifluoromethyl; each $R_5$ is, independently, halo, $C_1$-$C_4$ alkyl, or trifluoromethyl; m is 0, 1, or 2; and n is 0 or 1.

Exemplary duloxetine structural analogs are N-methyl-3-(1-naphthalenyloxy)-3-(3-thienyl)propanamine phosphate; N-methyl-3-(2-naphthalenyloxy)-3-(cyclohexyl)propanamine citrate; N,N-dimethyl-3-(4-chloro-1-naphthalenyloxy)-3-(3-furanyl)propanamine hydrochloride; N-methyl-3-(5-methyl-2-naphthalenyloxy)-3-(2-thiazolyl)propanamine hydrobromide; N-methyl-3-[3-(trifluoromethyl)-1-naphthalenyloxy]-3-(3-methyl-2-thienyl)propanamine oxalate; N-methyl-3-(6-iodo-1-naphthalenyloxy)-3-(4pyridyl)propanamine maleate; N,N-dimethyl-3-(1-naphthalenyloxy)-3-(cycloheptyl)propanamine formate; N,N-dimethyl-3-(2-naphthalenyloxy)-3-(2-pyridyl)propanamine; N-methyl-3-(1-naphthalenyloxy)-3-(2-furanyl)propanamine sulfate; N-methyl-3-(4-methyl-1-naphthalenyloxy)-3-(4-thiazolyl)propanamine oxalate; N-methyl-3-(2-naphthalenyloxy)-3-(2-thienyl)propanamine hydrochloride; N,N-dimethyl-3-(6-iodo-2-naphthalenyloxy)-3-(4-bromo-3-thienyl)propanamine malonate; N,N-dimethyl-3-(1-naphthalenyloxy)-3-(3-pyridyl)propanamine hydroiodide; N,N-dimethyl-3-(4-methyl-2-naphthalenyloxy)-3-(3-furanyl)propanamine maleate; N-methyl-3-(2-naphthalenyloxy)-3-(cyclohexyl)propanamine caprate; N-methyl-3-(6-n-propyl-1-naphthalenyloxy)-3-(3-isopropyl-2-thienyl)propanamine citrate; N,N-dimethyl-3-(2-methyl-1-naphthalenyloxy)-3-(4-thiazolyl)propanamine monohydrogen phosphate; 3-(1-naphthalenyloxy)-3-(5-ethyl-3-thienyl)propanamine succinate; 3-[3-(trifluoromethyl)-1-naphthalenyloxy]-3-(pyridyl)propanamine acetate; N-methyl-3-(6-methyl-1-naphthalenyl-3-(4-chloro-2-thienyl)propanamine tartrate; 3-(2-naphthalenyloxy)-3-(cyclopentyl)propanamine; N-methyl-3-(4-n-butyl-1-naphthalenyloxy)-3-(3-furanyl)propanamine methanesulfonate; 3-(2-chloro-1-naphthalenyloxy)-3-(5-thiazolyl)propanamine oxalate; N-methyl-3-(1-naphthalenyloxy)-3-(3-furanyl)propanamine tartrate; N,N-dimethyl-3-(phenoxy)-3-(2-furanyl)propanamine oxalate; N,N-dimethyl-3-[4-(trifluoromethyl)phenoxy]-3-(cyclohexyl)propanamine hydrochloride; N-methyl-3-(4-methylphenoxy)-3-(4-chloro-2-thienyl)propanamine propionate; N-methyl-3-(phenoxy)-3-(3-pyridyl)propanamine oxalate; 3-2-chloro-4-(trifluoromethyl)phenoxy]-3-(2-thienyl)propanamine; N,N-dimethyl-3-(3-methoxyphenoxy)-3-(3-bromo-2-thienyl)propanamine citrate; N-methyl-3-(4-bromophenoxy)-3-(4-thiazolyl)propanamine maleate; N,N-dimethyl-3-(2-ethylphenoxy)-3-(5-methyl-3-thienyl)propanamine; N-methyl-3-(2-bromophenoxy)-3-(3-thienyl)propanamine succinate; N-methyl-3-(2,6-dimethylphenoxy)-3-(3-methyl-2-thienyl)propanamine acetate; 3-[3-(trifluoromethyl)phenoxy]-3-(3-furanyl)propanamine oxalate; N-methyl-3-(2,5-dichlorophenoxy)-3-(cyclopentyl)propanamine; 3-[4-(trifluoromethyl)phenoxy]-3-(2-thiazolyl)propanamine; N-methyl-3-(phenoxy)-3-(5- methyl-2-thienyl)propanamine citrate; 3-(4-methylphenoxy)-3-(4-pyridyl)propanamine hydrochloride; N,N-dimethyl-3-(3-methyl-5-bromophenoxy)-3-(3-thienyl)propanamine; N-methyl-3-(3-n-propylphenoxy)-3-(2-thienyl)propanamine hydrochloride; N-methyl-3-(phenoxy)-3-(3-thienyl)propanamine phosphate; N-methyl-3-(4-methoxyphenoxy)-3-(cycloheptyl)propanamine citrate; 3-(2-chlorophenoxy)-3-(5-thiazolyl)propanamine propionate; 3-2-chloro-4-(trifluoromethyl)phenoxy]-3-(3-thienyl)propanamine oxalate; 3-(phenoxy)-3-(4-methyl-2-thienyl)propanamine; N,N-dimethyl-3-(4-ethylphenoxy)-3-(3-pyridyl)propanamine maleate; and N,N-dimethyl-3-[4-(trifluoromethyl)phenoxy]-3-(2-pyridyl)propanamine.

Structural analogs of milnacipram are those having the formula:

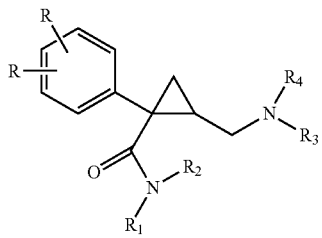

as well as pharmaceutically acceptable salts thereof, wherein each R, independently, represents hydrogen, bromo, chloro, fluoro, $C_{1-4}$ alkyl, $C_{1-4}$ alkoxy, hydroxy, nitro or amino; each of $R_1$ and $R_2$, independently, represents hydrogen, $C_{1-4}$ alkyl, $C_{6-12}$ aryl or $C_{7-14}$ alkylaryl, optionally substituted, preferably in para position, by bromo, chloro, or fluoro, or $R_1$ and $R_2$ together form a heterocycle having 5 or 6 members with the adjacent nitrogen atoms; $R_3$ and $R_4$ represent hydrogen or a $C_{1-4}$ alkyl group or $R_3$ and $R_4$ form with the adjacent nitrogen atom a heterocycle having 5 or 6 members, optionally containing an additional heteroatom selected from nitrogen, sulphur, and oxygen.

Exemplary milnacipram structural analogs are 1-phenyl 1-aminocarbonyl 2-dimethylaminomethyl cyclopropane; 1-phenyl 1-dimethylaminocarbonyl 2-dimethylaminomethyl cyclopropane; 1-phenyl 1-ethylaminocarbonyl 2-dimethylaminomethyl cyclopropane; 1-phenyl 1-diethylaminocarbonyl 2-aminomethyl cyclopropane; 1-phenyl 2-dimethylaminomethyl N-(4'-chlorophenyl)cyclopropane carboxamide; 1-phenyl 2-dimethylaminomethyl N-(4'-chlorobenzyl)cyclopropane carboxamide; 1-phenyl 2-dimethylaminomethyl N-(2-phenylethyl)cyclopropane carboxamide; (3,4-dichloro-1-phenyl)2-dimethylaminomethyl N,N-dimethylcyclopropane carboxamide; 1-phenyl 1-pyrrolidinocarbonyl 2-morpholinomethyl cyclopropane; 1-p-chlorophenyl 1-aminocarbonyl 2-aminomethyl cyclopropane; 1-orthochlorophenyl 1-am inocarbonyl 2-dimethylaminomethyl cyclopropane; 1-p-hydroxyphenyl 1-am inocarbonyl 2-dimethylaminomethyl cyclopropane; 1-p-nitrophenyl 1-dimethylaminocarbonyl 2-dimethylaminomethyl cyclopropane; 1-p-aminophenyl 1-dimethylaminocarbonyl 2-dimethylaminomethyl cyclopropane; 1-p-tolyl 1-methylaminocarbonyl 2-dimethylaminomethyl cyclopropane; 1-p-methoxyphenyl 1-aminomethylcarbonyl 2-aminomethyl cyclopropane; and pharmaceutically acceptable salts of any thereof.

Structural analogs of sibutramine are those compounds having the formula:

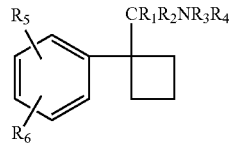

as well as pharmaceutically acceptable salts thereof, wherein $R_1$ is $C_{1-6}$ alkyl, $C_{2-6}$ alkenyl, $C_{2-6}$ alkynyl, $C_{3-7}$ cycloalkyl, cycloalkylalkyl, or optionally substituted phenyl (substitutents include halogen and $C_{1-3}$ alkyl); $R_2$ is H or $C_{1-3}$ alkyl; each of $R_3$ and $R_4$ is, independently, H, formyl, or $R_3$ and $R_4$ together with the nitrogen atom form a heterocyclic ring system; each of $R_5$ and $R_6$ is, independently, H, halogen, $CF_3$, $C_{1-3}$ alkyl, $C_{1-3}$ alkoxy, $C_{1-3}$ alkylthio, or $R_6$ together with the carbon atoms to which they are attached form a second benzen ring.

Exemplary sibutramine structural analogs are i-[1-(3,4-dichlorophenyl)cyclobutyl]ethylamine hydrochloride; N-methyl-1-[1-(3,4-dichlorophenyl)cyclobutyl]ethylamine hydrochloride; N,N-dimethyl-1-[1-(3,4-dichlorophenyl)cyclobutyl]ethylamine hydrochloride; 1-[1-(4-iodophenyl)cyclobutyl]ethylamine hydrochloride; N-methyl-1-[1-(4-iodophenyl)cyclobutyl]ethylamine hydrochloride; N,N-dimethyl-1-[1-(4-iodophenyl)cyclobutyl]ethylamine hydrochloride; N-methyl-1-[1-(2-naphthyl)cyclobutyl]ethylamine hydrochloride; N,N-dimethyl-1-[1-(4-chloro-3-trifluoromethylphenyl)cyclobutyl]ethylamine hydrochloride; i-[1-(4-chlorophenyl)cyclobutyl]butylamine hydrochloride; N-methyl-1-[1-(4-chlorophenyl)cyclobutyl]butylamine hydrochloride; N,N-dimethyl-1-[1-(4-chlorophenyl)cyclobutyl]butyl amine hydrochloride; 1-[1-(3,4-dichlorophenyl)cyclobutyl]butylamine hydrochloride; N-methyl-1-[1-(3,4-dichlorophenyl)cyclobutyl]butylamine hydrochloride; N,N-dimethyl-1-[1-(3,4-dichlorophenyl)cyclobutyl]butylamine hydrochloride; 1-[1-(4-biphenylyl)cyclobutyl]butylamine hydrochloride; N,N-dimethyl-1-[1-(4-biphenylyl)cyclobutyl]butylamine hydrochloride; 1-[1-(4-chloro-3-fluorophenyl)cyclobutyl]butylamine hydrochloride; N-formyl-1-[1-(4-chloro-3-fluorophenyl)cyclobutyl]butylamine; 1-[1-(3-chloro-4-methylphenyl)cyclobutyl]butylamine hydrochloride; N-formyl-1-[1-phenylcyclobutyl]butylamine; 1-[1-(3-trifluoromethylphenyl)cyclobutyl]butylamine hydrochloride; 1-[1-(naphth-2-yl)cyclobutyl]butylamine hydrochloride; 1-[1-(6-chloronaphth-2-yl)cyclobutyl]butylamine; N-methyl-1-[1-(4-chlorophenyl)cyclobutyl]-2-methylpropylamine hydrochloride; 1-[1-(4-chlorophenyl)cyclobutyl]pentylamine hydrochloride; N-methyl-1-[1-(4-chlorophenyl)cyclobutyl]pentylamine hydrochloride; N,N-dimethyl-1-[1-phenylcyclobutyl]-3-methylbutylamine hydrochloride; 1-[1-(4-chlorophenyl)cyclobutyl]-3-methylbutylamine hydrochloride; N-methyl-1-[1-(4-chlorophenyl)cyclobutyl]-3-methylbutylamine hydrochloride; N,N-dimethyl-1-[1-(4-chlorophenyl)cyclobutyl]-3-methylbutylamine hydrochloride; N-formyl-1-[1-(4-chlorophenyl)cyclobutyl]-3-methylbutylamine; N,N-dimethyl-1-[1-(3,4-dichlorophenyl)cyclobutyl]-3-methylbutylamine hydrochloride; N-methyl-1-[1-(naphth-2-yl)cyclobutyl]-3-methylbutylamine hydrochloride; N-methyl-1-[1-(3,4-dimethylphenyl)cyclobutyl]-3-methylbutylamine hydrochloride; [1-(4-chlorophenyl)cyclobutyl](cyclopropyl)methylamine hydrochloride; N-methyl-[1-(4-chlorophenyl)cyclobutyl](cyclopentyl)methylamine hydrochloride; [1-(4-chlorophenyl)cyclobutyl](cyclohexyl)methylamine hydrochloride; N-methyl-[1-(4-chlorophenyl)cyclobutyl](cyclohexyl)methylamine hydrochloride; [1-(3,4-dichlorophenyl)cyclobutyl](cyclohexyl)methylamine hydrochloride; N-methyl-[1-(3,4-dichlorophenyl)cyclobutyl](cyclohexyl)methylamine hydrochloride; [1-(4-chlorophenyl)cyclobutyl](cycloheptyl)methylamine hydrochloride; 1-[1-(4-chlorophenyl)cyclobutyl]-2-cyclopropylethylamine hydrochloride; N,N-dimethyl-1-[1-(4-chlorophenyl)cyclobutyl]-2-cyclohexylethylamine hydrochloride; α-[1-(4-chlorophenyl)cyclobutyl]benzylamine hydrochloride; N-methyl-α-[1-(4-chlorophenyl)cyclobutyl]benzylamine hydrochloride; 1-[1-(4-chloro-2-fluorophenyl)cyclobutyl]butylamine; N,N-dimethyl-1-[1-(4-chloro-2-fluorophenyl)cyclobutyl]butylamine hydrochloride; N-ethyl-1-[1-(3,4-dichlorophenyl)cyclobutyl]ethylamine hydrochloride; and N,N-diethyl-1-[1-(3,4-dichlorophenyl)cyclobutyl]ethylamine hydrochloride.

Structural analogs of nefazodone are those compounds having the formula:

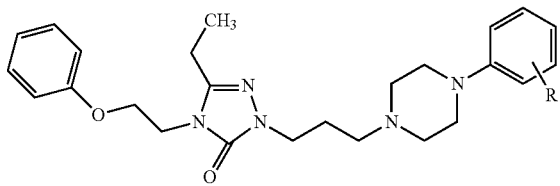

as well as pharmaceutically acceptable salts thereof, wherein R is halogen.

A particular embodiment refers to the combination of the invention comprising 4-{2-[5-methyl-1-(naphthalen-2-yl)-1H-pyrazol-3-yloxy]ethyl}morpholine or a pharmaceutically acceptable salt, isomer, prodrug or solvate thereof and a SNRI selected from the group consisting of venlafaxine, desvenlafaxine, duloxetine, milnacipram, levomilnacipram, sibutramine, nefazodone and bicifadine, or a pharmaceutically acceptable salt, isomer, prodrug or solvate thereof.

A more particular embodiment refers to the combination of the invention comprising 4-{2-[5-methyl-1-(naphthalen-2-yl)-1H-pyrazol-3-yloxy]ethyl}morpholine hydrochloride and a SNRI selected from the group consisting of venlafaxine, desvenlafaxine, duloxetine, milnacipram, levomilnacipram, sibutramine, nefazodone and bicifadine or a pharmaceutically acceptable salt, isomer, prodrug or solvate thereof.

A preferred embodiment refers to the synergistic combination of the invention comprising 4-{2-[5-methyl-1-(naphthalen-2-yl)-1H-pyrazol-3-yloxy]ethyl}morpholine or a pharmaceutically acceptable salt, isomer, prodrug or solvate thereof and venlafaxine or a pharmaceutically acceptable salt thereof such as venlafaxine hydrochloride.

A more preferred embodiment refers to the synergistic combination of the invention comprising 4-{2-[5-methyl-1-(naphthalen-2-yl)-1H-pyrazol-3-yloxy]ethyl}morpholine hydrochloride and venlafaxine or a pharmaceutically acceptable salt thereof such as venlafaxine hydrochloride.

Another preferred embodiment refers to the synergistic combination of the invention comprising 4-{2-[5-methyl-1-(naphthalen-2-yl)-1H-pyrazol-3-yloxy]ethyl}morpholine or a pharmaceutically acceptable salt, isomer, prodrug or solvate thereof and duloxetine or a pharmaceutically acceptable salt thereof such as duloxetine hydrochloride.

Another more preferred embodiment refers to the synergistic combination of the invention comprising 4-{2-[5-methyl-1-(naphthalen-2-yl)-1H-pyrazol-3-yloxy]ethyl}morpholine hydrochloride and duloxetine or a pharmaceutically acceptable salt thereof such as duloxetine hydrochloride.

The present invention refers also to medicaments or pharmaceutical compositions comprising at least one Sigma ligand of general formula (I) as defined above, or a pharmaceutically acceptable salt, isomer, prodrug or solvate thereof, and at least one SNRI combined jointly or separately, together with at least a pharmaceutically acceptable excipient.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

The pharmaceutical composition according to the present invention can be adapted to any form of administration, be it orally or parenterally, for example pulmonarily, nasally, rectally and/or intravenously. Therefore, the formulation according to the present invention may be adapted for topical or systemic application, particularly for dermal, subcutaneous, intramuscular, intra-articular, intraperitoneal, pulmonary, buccal, sublingual, nasal, percutaneous, vaginal, oral or parenteral application. The preferred form of rectal application is by means of suppositories.

Suitable preparations for oral applications are tablets, pills, chewing gums, capsules, granules, drops or syrups. Suitable preparations for parenteral applications are solutions, suspensions, reconstitutable dry preparations or sprays.

The combination of the invention may be formulated as deposits in dissolved form or in patches, for percutaneous application. Skin applications include ointments, gels, creams, lotions, suspensions or emulsions.

The combination of the invention may be formulated for its simultaneous, separate or sequential administration, with at least a pharmaceutically acceptable excipient. This has the implication that the combination of the Sigma ligand of general formula (I) and the SNRI may be administered:

a) As a combination that is being part of the same medicament formulation, both being then administered always simultaneously.

b) As a combination of two units, each with one of them giving rise to the possibility of simultaneous, sequential or separate administration. In a particular embodiment, the Sigma ligand of general formula (I) is independently administered from the SNRI (i.e in two units) but at the same time. In another particular embodiment, the sigma ligand of general formula (I) is administered first, and then the SNRI is separately or sequentially administered. In yet another particular embodiment, the SNRI is administered first, and then the Sigma ligand of general formula (I) is administered, separately or sequentially, as defined.

In a particular embodiment of the present invention, the pain is selected from central and peripheral neuropathic pain, allodynia, causalgia, hyperalgesia, hyperesthesia, hyperpathia, neuralgia, neuritis or neuropathy. More preferably, the pain is peripheral neuropathic pain, hyperalgesia or allodynia.

"Neuropathic pain" is defined by the IASP as "pain initiated or caused by a primary lesion or dysfunction in the nervous system" (IASP, Classification of chronic pain, $2^{nd}$ Edition, IASP Press (1994), 210). For the purpose of this invention this term is to be treated as synonymous to "Neurogenic Pain" which is defined by the IASP as "pain initiated or caused by a primary lesion, dysfunction or transitory perturbation in the peripheral or central nervous system".

According to the IASP "peripheral neuropathic pain" is defined as "a pain initiated or caused by a primary lesion or dysfunction in the peripheral nervous system" and "peripheral neurogenic pain" is defined as "a pain initiated or caused by a primary lesion, dysfunction or transitory perturbation in the peripheral nervous system" (IASP, Classification of chronic pain, $2^{nd}$ Edition, IASP Press (1994), 213).

According to the IASP "allodynia" is defined as "a pain due to a stimulus which does not normally provoke pain" (IASP, Classification of chronic pain, $2^{nd}$ Edition, IASP Press (1994), 210).

According to the IASP "causalgia" is defined as "a syndrome of sustained burning pain, allodynia and hyperpathia after a traumatic nerve lesion, often combined with vasomotor and sudomotor dysfunction and later trophic changes" (IASP, Classification of chronic pain, $2^{nd}$ Edition, IASP Press (1994), 210).

According to the IASP "hyperalgesia" is defined as "an increased response to a stimulus which is normally painful" (IASP, Classification of chronic pain, $2^{nd}$ Edition, IASP Press (1994), 211).

According to the IASP "hyperesthesia" is defined as "increased sensitivity to stimulation, excluding the senses" (IASP, Classification of chronic pain, $2^{nd}$ Edition, IASP Press (1994), 211).

According to the IASP "hyperpathia" is defined as "a painful syndrome characterized by an abnormally painful reaction to a stimulus, especially a repetitive stimulus, as well as an increased threshold" (IASP, Classification of chronic pain, $2^{nd}$ Edition, IASP Press (1994), 212).

The IASP draws the following difference between "allodynia", "hyperalgesia" and "hyperpathia" (IASP, Classification of chronic pain, $2^{nd}$ Edition, IASP Press (1994), 212):

| | | |
|---|---|---|
| Allodynia | Lowered threshold | Stimulus and response mode differ |
| Hyperalgesia | Increased response | Stimulus and response rate are the same |
| Hyperpathia | Raised threshold Increased response | Stimulus and response rate may be the same or different |

According to the IASP "neuralgia" is defined as "pain in the distribution of a nerve or nerves" (IASP, Classification of chronic pain, $2^{nd}$ Edition, IASP Press (1994), 212).

According to the IASP "neuritis" is defined as "inflammation of a nerve or nerves" (IASP, Classification of chronic pain, $2^{nd}$ Edition, IASP Press (1994), 212).

According to the IASP "neuropathy/neuritis" is defined as "a disturbance of function or pathological change in a nerve: in one nerve mononeuropathy, in several nerves mononeuropthy multiplex, if diffuse and bilateral, polyneuropathy" (IASP, Classification of chronic pain, $2^{nd}$ Edition, IASP Press (1994), 212).

Another aspect of the invention is a method of treatment and/or prophylaxis of a patient suffering from pain, or likely to suffer pain, the method comprising administering to the patient in need of such a treatment or prophylaxis a therapeutically effective amount of a combination comprising at least one Sigma ligand of general formula (I) as defined above, or a pharmaceutically acceptable salt, isomer, prodrug or solvate thereof, and at least one SNRI.

By an "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination (i.e. Sigma ligand of general formula (I) or SNRI) is the amount of that compound that is effective to provide the desired effect when used in combination with the other component of the combination (i.e. SNRI or Sigma ligand of general formula (I)). The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation.

According to the present invention the dosage of the SNRI can be reduced when combined with a Sigma ligand of general formula (I), and therefore attaining the same analgesic effect with a reduced dosage, and thus attenuating the adverse effects.

For example, the dosage regime that must be administered to the patient will depend on the patient's weight, the type of application, the condition and severity of the disease. A preferred dosage regime comprises an administration of a Sigma compound of general formula (I) within a range of 0.5 to 100 mg/kg and of the SNRI from 0.15 to 15 mg/kg. The administration may be performed once or in several occasions.

Having described the present invention in general terms, it will be more easily understood by reference to the following examples which are presented as an illustration and are not intended to limit the present invention.

EXAMPLES

Example 1. Synthesis of 4-{2-[5-Methyl-1-(naphthalen-2-yl)-1H-pyrazol-3-yloxy]ethyl}morpholine (compound 63) and its hydrochloride salt

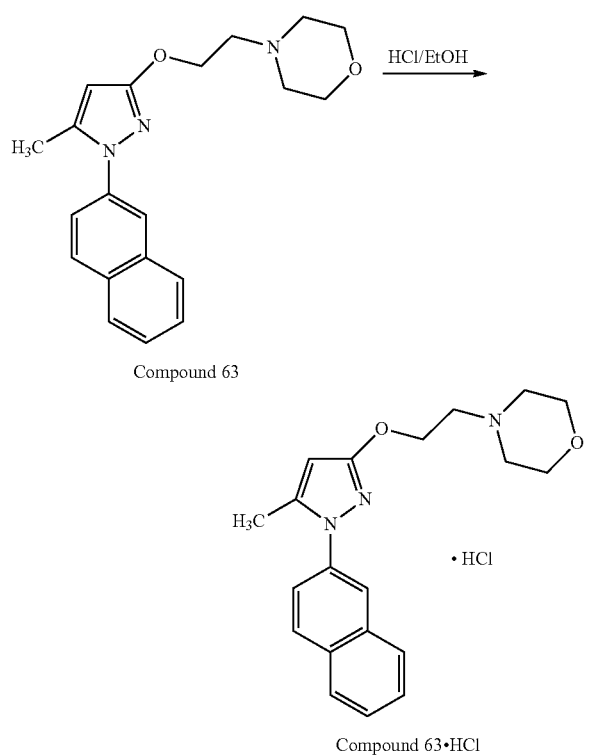

Compound 63 can be prepared as disclosed in the previous application WO2006/021462. Its hydrochloride can be obtained according the following procedure: Compound 63 (6.39 g) was dissolved in ethanol saturated with HCl, the mixture was stirred then for some minutes and evaporated to dryness. The residue was crystallized from isopropanol. The mother liquors from the first crystallization afforded a second crystallization by concentrating. Both crystallizations taken together yielded 5.24 g (63%) of the corresponding hydrochloride salt (m.p.=197-199° C.)

$^1$H-NMR (DMSO-$d_6$) δ ppm: 10.85 (bs, 1H), 7.95 (m, 4H), 7.7 (dd, J=2.2, 8.8 Hz, 1H), 7.55 (m, 2H), 5.9 (s, 1H), 4.55 (m, 2H), 3.95 (m, 2H), 3.75 (m, 2H), 3.55-3.4 (m, 4H), 3.2 (m, 2H), 2.35 (s, 3H).

HPLC purity: 99.8%

Example 2. Assessment of Analgesia in the Treatment Post-Operative Pain 2.1 General Protocol.

The induction of anesthesia in rats was performed with 3% isofluran for veterinary use, employing an Ohmeda vaporizer and an anesthesia chamber. Anesthesia was kept during the surgical operation by a tube which directs the isofluran vapors to the animal's snout. Once the rats were anesthetized, they were laid down in a prone position and their right hind paws were cleaned out with alcohol.

Then, a skin incision in the hindpaw of about 10 mm was made by means of a scalpel, starting about 5 mm from the heel and extending toward the toes. Fascia was located and by means of curve scissors muscle was elevated and a longitudinal incision of about 5 mm was made, thus the muscle origin and insertion remained intact. The skin of the paw was stitched with a suturing stitch with breaded silk (3.0) and the wound was cleaned out with povidone.

The assessment was performed 30 minutes after the administration of product and always 4 hours after the plantar incision. The analysis was carried out evaluating the mechanical allodynia. It was tested using von Frey filaments: Animals were placed in methacrylate cylinders on an elevated surface, with metallic mesh floor perforated in order to apply the filaments. After an acclimation period of about 30 minutes within the cylinders, both hindpaws were stimulated (the injured and the non-injured paw, serving the latter as control), starting with the lowest force filament (0.4 g) and reaching a 15 g filament. The animal's response to pain was manifested by the withdrawal of the paw as a consequence of the painful stimulus caused by a filament.

2.2 Combination of Compound 63.HCl and Venlafaxine

The efficacy of the combined use of venlafaxine and compound 63.HCl was tested at different doses of compound 63.HCl (5, 10, 20, 40 and 80 mg/kg), while the venlafaxine dose remained constant (2.5 mg/kg). The administrations were performed 3.5 hours after surgery. The treated subjects were tested according to the mechanical allodynia protocol above (FIG. 1).

2.3 Combination of Compound 63.HCl and Duloxetine

The efficacy of the combined use of duloxetine and compound 63.HCl was tested at different doses of compound 63.HCl (10, 20, 40 and 80 mg/kg), while the duloxetine dose remained constant (0.625 mg/kg). The administrations were performed 3.5 hours after surgery. The treated subjects were tested according to the mechanical allodynia protocol above (FIG. 2).

CONCLUSIONS

As shown in FIG. 1, compound 63.HCl produced a dose dependent effect with a maximum effect of 43%. The Figure also shows Venlafaxine, in a sub-active dose (2.5 mg/kg), which produced a non-significant effect. Finally, it can be seen that the combination Venlafaxine (in a sub-active dose) and compound 63.HCl produced a dose-dependent effect with ED50=14.5 mg/kg. Therefore, compound 63.HCl and Venlafaxine act synergically to produce analgesia in the treatment of post-operative pain.

Figure 2:
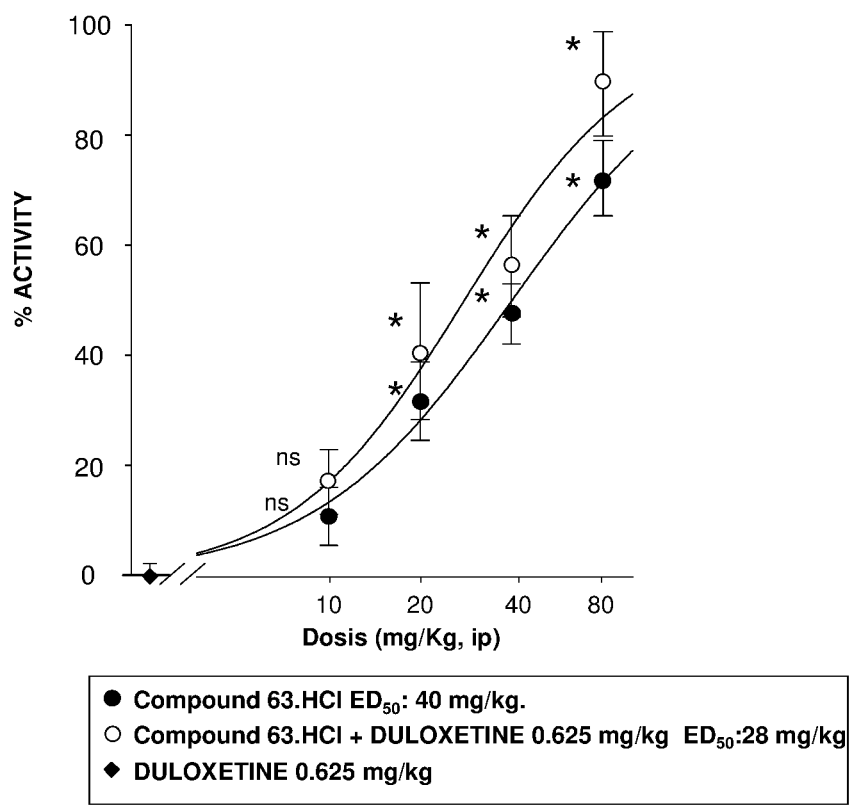
FIG. 2: Potentiation of a subactive dose of duloxetine (0.625 mg/kg) by compound 63.HCl (10, 20, 40 and 80 mg/kg) in the mechanical allodynia of the post-operative pain model in rats. n=10, *: p<0.05; ns: p>0.05 Dunnett, compound 63.HCl+Duloxetine vs. Duloxetine.

As shown in FIG. 2, compound 63.HCl produced a dose dependent effect with an ED50 of 40 mg/kg. The Figure also shows Duloxetine, in a sub-active dose (0.625 mg/kg), which produced a non-significant effect. Finally, it can be seen that the combination Duloxetine (in a sub-active dose) and compound 63.HCl produced a dose-dependent effect with ED50=28 mg/kg. Therefore, compound 63 HCl and Duloxetine act synergically to produce analgesia in the treatment of post-operative pain.

REFERENCES

Cobos, E. J., Entrena, J. M., Nieto, F. R., Cendan, C. M., Del Pozo, E. Pharmacology and therapeutic potential of Sigma(1) receptor ligands. *Curr. Neuropharmacol.* 2008; 6, 344-366.

Maurice, T., Su, T. P., The pharmacology of Sigma-1 receptors. *Pharmacol. Ther.* 2009; 124, 195-206.

Merskey et al.; "Part III: Pain Terms, A Current List with Definitions and Notes on Usage" (pp 209-214) Classification of Chronic Pain, Second Edition, IASP Task Force on Taxonomy, edited by H. Merskey and N. Bogduk, IASP Press, Seattle, ©1994.

Romero, L., Zamanillo, D., Nadal, X., Sanchez-Arroyos, R., Rivera-Arconada, I., Dordal, A., Montero, A., Muro, A., Bura, A., Segales, C., Laloya, M., Hernandez, E., Portillo-Salido, E., Escriche, M., Codony, X., Encina, G., Burgueno, J., Merlos, M., Baeyens, J., Giraldo, J., Lopez-Garcia, J., Maldonado, R., Plata-Salaman, C., Vela, J. Pharmacological properties of S1RA, a new Sigma-1 receptor antagonist that inhibits neuropathic pain and activity-induced spinal sensitization. *Br. J. Pharmacol.* 2012; doi: 10.1111/j.1476-5381.

Sussman. SNRIs Versus SSRIs: Mechanisms of Action in Treating Depression and Painful Physical Symptoms. *J. Clin. Psychiatry;* 2003

Marks, D. M., Shah, M. J., Patkar, A. A., Masand, P. S., Park, G-Y and Pae, Ch-U Serotonin-Norepinephrine Reuptake Inhibitors for Pain Control: Premise and Promise *Current Neuropharmacology,* 2009, 7, 331-336

The invention claimed is:

1. A synergistic combination comprising at least one Serotonin-Norepinephrine Reuptake Inhibitor (SNRI) and at least 4-[2-[5-Methyl-1-(naphthalen-2-yl)-1H-

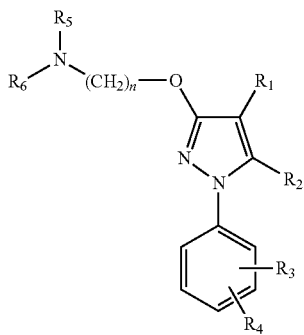

(I)

pyrazol-3-yloxy]ethyl}morpholine or a pharmaceutically acceptable salt, isomer, or solvate thereof;

wherein the SNRI is selected from the group consisting of venlafaxine, desvenlafaxine and duloxetine or a pharmaceutically acceptable salt, isomer, or solvate thereof.

2. The synergistic combination according to claim 1, wherein the combination comprises 4-{2-[5-methyl-1-(naphthalen-2-yl)-1H-pyrazol-3 yloxy]ethyl}morpholine hydrochloride.

3. The synergistic combination according to claim 1, wherein the SNRI is selected from the group consisting of venlafaxine and duloxetine, or a pharmaceutically acceptable salt, isomer, or solvate thereof.

4. The synergistic combination according to claim 3, wherein the SNRI comprises venlafaxine or a pharmaceutically acceptable salt, isomer, or solvate thereof.

5. The synergistic combination according to claim 3, wherein the SNRI comprises duloxetine or a pharmaceutically acceptable salt, isomer, or solvate or thereof.

6. The synergistic combination according to claim 1, wherein the combination comprises 4-{2-[5-methyl-1-(naphthalen-2-yl)-1H-pyrazol-3-yloxy]ethyl}morpholine or a pharmaceutically acceptable salt thereof and venlafaxine or a pharmaceutically acceptable salt thereof.

7. The synergistic combination according to claim 1, wherein the combination comprises 4-{2-[5-methyl-1-(naphthalen-2-yl)-1H-pyrazol-3-yloxy]ethyl}morpholine or a pharmaceutically acceptable salt thereof and duloxetine or a pharmaceutically acceptable salt thereof.

8. A method of treatment and/or prophylaxis of a patient suffering from pain, or likely to suffer pain, the method comprising administering to the patient in need of such a treatment or prophylaxis a therapeutically effective amount of a synergistic combination according to claim 1.

9. The method according to claim 8, wherein the analgesic effect of the SNRI is potentiated in the synergistic combination.

10. The synergistic combination according to claim 1, wherein an analgesic effect of the SNRI is potentiated in the synergistic combination.

11. The synergistic combination according to claim 9, wherein the analgesic effect of the SNRI is potentiated by the 4-[2-[5-Methyl-1-(naphthalen-2-yl)-1H-pyrazol-3-yloxy]ethyl}morpholine.

* * * * *